(12) United States Patent
Man et al.

(10) Patent No.: US 9,303,240 B2
(45) Date of Patent: *Apr. 5, 2016

(54) CLEANING COMPOSITIONS AND EMULSIONS OR MICROEMULSIONS EMPLOYING EXTENDED CHAIN NONIONIC SURFACTANTS

(71) Applicant: ECOLAB USA INC., St. Paul, MN (US)

(72) Inventors: Victor Fuk-Pong Man, St. Paul, MN (US); Yvonne Marie Killeen, South St. Paul, MN (US); Steven E. Lentsch, St. Paul, MN (US); Michael Charles Denoma, Vadnais Heights, MN (US)

(73) Assignee: ECOLAB USA INC, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/178,515

(22) Filed: Feb. 12, 2014

(65) Prior Publication Data

US 2014/0196220 A1    Jul. 17, 2014

Related U.S. Application Data

(63) Continuation of application No. 12/884,638, filed on Sep. 17, 2010, now Pat. No. 8,697,622.

(51) Int. Cl.

| | |
|---|---|
| *C11D 17/00* | (2006.01) |
| *A61K 8/06* | (2006.01) |
| *A61K 8/37* | (2006.01) |
| *A61K 8/39* | (2006.01) |
| *A61K 8/46* | (2006.01) |
| *A61K 8/86* | (2006.01) |
| *A61Q 19/10* | (2006.01) |
| *C11D 1/722* | (2006.01) |
| *C11D 1/825* | (2006.01) |
| *D06L 1/12* | (2006.01) |
| *D06L 1/16* | (2006.01) |
| *D06L 1/20* | (2006.01) |
| *B01F 17/00* | (2006.01) |
| *C11D 1/66* | (2006.01) |
| *C11D 1/72* | (2006.01) |
| *C11D 1/74* | (2006.01) |

(52) U.S. Cl.
CPC ............ *C11D 17/0021* (2013.01); *A61K 8/068* (2013.01); *A61K 8/375* (2013.01); *A61K 8/39* (2013.01); *A61K 8/463* (2013.01); *A61K 8/86* (2013.01); *A61Q 19/10* (2013.01); *B01F 17/0085* (2013.01); *C11D 1/722* (2013.01); *C11D 1/825* (2013.01); *D06L 1/12* (2013.01); *D06L 1/16* (2013.01); *D06L 1/20* (2013.01); *A61K 2800/596* (2013.01); *C11D 1/667* (2013.01); *C11D 1/72* (2013.01); *C11D 1/721* (2013.01); *C11D 1/74* (2013.01)

(58) Field of Classification Search
CPC .................................................. C11D 17/0021

USPC .......................................... 510/214, 267, 354
See application file for complete search history.

(56) References Cited

U.S. PATENT DOCUMENTS

| | | | |
|---|---|---|---|
| 3,871,898 A | 3/1975 | Reinert et al. | |
| 4,492,646 A | 1/1985 | Welch | |
| 5,082,584 A | 1/1992 | Loth et al. | |
| 5,376,310 A | 12/1994 | Cripe et al. | |
| 5,393,468 A | 2/1995 | Erilli et al. | |
| 5,597,507 A * | 1/1997 | Garrett et al. | 510/340 |
| 5,688,930 A | 11/1997 | Bertho et al. | |
| 5,707,948 A | 1/1998 | Evers et al. | |
| 5,888,957 A | 3/1999 | Durbut et al. | |
| 5,994,283 A | 11/1999 | Durbut et al. | |
| 6,136,769 A | 10/2000 | Asano et al. | |
| 6,156,712 A | 12/2000 | Stringer et al. | |
| 6,228,829 B1 | 5/2001 | Vinson et al. | |
| 6,254,859 B1 * | 7/2001 | Shapiro et al. | 424/70.1 |

(Continued)

FOREIGN PATENT DOCUMENTS

| | | |
|---|---|---|
| EP | 0368146 A2 | 5/1990 |
| EP | 0573341 B1 | 7/1998 |

(Continued)

OTHER PUBLICATIONS

Barber, J.A.S., et al., "Fluorescent tracer technique for measuring the quantity of pesticide deposited to soil following spray applications," Elsevier, Crop Protection 22 (2003) pp. 15-21.
Bergervoet, P.W.M., et al., "Application of the forensic Luminol for blood in infection control," Elsevier, Journal of Hospital Infection (2008) 68, pp. 329-333.
Carling, Philip C., et al., "Improved Cleaning of Patient Rooms Using a New Targeting Method," Brief Report, CID 2006:42 (Feb. 1), pp. 385-388.
Charoensaeng, Ampira, et al, "Solubilization and Adsolubilization of Polar and Nonpolar Organic Solutes by Linker Molecules and Extended Surfactants," Springer AOCS, J. Surfact. Deterg. (2009) 12, pp. 209-217.
Do, Linh D., et al., "Environmentally Friendly Vegetable Oil Microemulsions Using Extended Surfactants and Linkers," Springer AOCS, J. Surfact. Deterg. (2009) 12, pp. 91-99.
Griffith, C.J., et al. "An evaluation of hospital cleaning regimes and standards," The Hospital Infection Society, Journal of Hospital Infection (2000) 45, pp. 19-28.

(Continued)

*Primary Examiner* — Nicole M Buie-Hatcher
*Assistant Examiner* — M. Reza Asdjodi
(74) *Attorney, Agent, or Firm* — McKee, Voorhees & Sease, PLC

(57) ABSTRACT

Synergistic combinations of extended chain surfactants and co-surfactants, emulsions or microemulsions and cleaning compositions incorporating the same are provided. In certain embodiments a surfactant system is disclosed which includes extended nonionic surfactants, and a linker surfactant. This system forms stable emulsions or microemulsions with oils, including non-trans fats and fatty acids and these emulsions or microemulsions are stable, irreversible and can be created at low temperature. The cleaning compositions may include the surfactant system alone, a stable emulsion or microemulsion with oil and the surfactant system, a pre-spotter or other pre-treatment or soft surface and hard surface cleaning compositions comprising the surfactant combination.

21 Claims, 5 Drawing Sheets

(56) References Cited

U.S. PATENT DOCUMENTS

| | | | |
|---|---|---|---|
| 6,274,874 B1 | 8/2001 | Sidhu | |
| 6,277,808 B1 | 8/2001 | Tcheou et al. | |
| 6,472,364 B1 | 10/2002 | Heltovics | |
| 6,511,954 B1 | 1/2003 | Wilbur et al. | |
| 6,589,926 B1 | 7/2003 | Vinson et al. | |
| 6,613,726 B1 | 9/2003 | Gagliardi et al. | |
| 6,740,627 B1 | 5/2004 | Clarke et al. | |
| 6,827,795 B1 | 12/2004 | Kasturi et al. | |
| 7,037,884 B2 | 5/2006 | Man | |
| 7,288,512 B2* | 10/2007 | Boone et al. | 510/418 |
| 7,467,633 B2* | 12/2008 | Smith et al. | 134/25.2 |
| 8,361,950 B2* | 1/2013 | Man et al. | 510/276 |
| 2001/0026942 A1 | 10/2001 | Carpenter et al. | |
| 2002/0193268 A1 | 12/2002 | Embleton et al. | |
| 2003/0087787 A1 | 5/2003 | Man et al. | |
| 2003/0096726 A1* | 5/2003 | Smith et al. | 510/424 |
| 2003/0139313 A1 | 7/2003 | Turner et al. | |
| 2005/0020466 A1 | 1/2005 | Man et al. | |
| 2005/0049168 A1* | 3/2005 | Yan et al. | 510/421 |
| 2006/0165739 A1* | 7/2006 | Komesvarakul et al. | 424/401 |
| 2006/0211593 A1* | 9/2006 | Smith et al. | 510/424 |
| 2007/0054827 A1 | 3/2007 | Cheung | |
| 2007/0143032 A1 | 6/2007 | Wieringa et al. | |
| 2008/0207981 A1 | 8/2008 | Hoag et al. | |
| 2009/0183877 A1* | 7/2009 | Quintero et al. | 166/300 |
| 2009/0208051 A1 | 8/2009 | Emo et al. | |
| 2009/0223635 A1 | 9/2009 | Lawless | |
| 2009/0261270 A1 | 10/2009 | Carling | |
| 2011/0112007 A1* | 5/2011 | Hodge et al. | 510/405 |
| 2011/0112008 A1* | 5/2011 | Hodge et al. | 510/405 |

FOREIGN PATENT DOCUMENTS

| | | |
|---|---|---|
| JP | 63073140 A | 4/1988 |
| JP | 1100442 A | 4/1989 |
| JP | 10292199 A | 11/1998 |
| JP | 2001246339 | 9/2001 |
| JP | 2009210514 | 9/2009 |
| WO | WO 9732962 | 9/1997 |
| WO | WO 9927054 | 6/1999 |
| WO | WO 0068348 | 11/2000 |
| WO | WO 2007064525 A1 | 6/2007 |
| WO | WO 2007101470 A1 | 9/2007 |
| WO | WO 2010086821 A2 | 8/2010 |

OTHER PUBLICATIONS

Hartel, Peter G., et al., "Exposing water samples to ultraviolet light improves fluorometry for detecting human fecal contamination," Elsevier, Water Research (2007) pp. 3629-3642.

Lipscomb, I.P., et al., "Rapid method for the sensitive detection of protein contamination on surgical instruments," Elsevier, Journal of Hospital Infection (2006) 62, pp. 141-148.

Lu, Y.F., et al., "Laser surface cleaning and real-time monitoring," ALT '99 International Conference on Advanced Laser Technologies, SPIE vol. 4070 (2000), pp. 331-337.

Mori, F., et al., "Equilibrium and dynamic behavior of a system containing a mixture of anionic and nonionic surfactants," Progress in Colloid & Polymer Science (1990) 82, pp. 114-121.

Phan, Tri T., et al., "Microemulsion-Based Vegetable Oil Detergency Using an Extended Surfactant," Springer AOCS, J. Surfact. Deterg (2010) 13, pp. 313-319.

Pyrek, Kelly M., "Hospitals Can Learn from CSI Sleuthing Methods," Virgo Publishing (2011), posted on Jun. 9, 2008 at website: http://www.infectioncontroltoday.com/.

Salo, Satu, et al., "Cleaning validation of fermentation tanks," Elsevier, Food and Bioproducts Processing 86 (2008) pp. 204-210.

Wisniewski, Karen, "Specialty Liquid Household Surface Cleaners," Research & Development, Global Technology, Colgate-Palmolive Company, pp. 463-512.

Witthayapanyanon, Anuradee, et al., "Interfacial Properties of Extended-Surfactant-Based Microemulsions and Related Macroemulsions," Springer AOCS, J. Surfact. Deterg. (2010) 13, pp. 127-134.

Zhang, Hui, et al., "Lauryl Alcohol and Amine Oxide as Foam Stabilizers in the Presence of Hardness and Oily Soil," Journal of Surfactants and Detergents, vol. 8, No. 1 (Jan. 2005), pp. 99-107.

Website of "Cleanser alcohol hand rub training gel Fluroescent gel 500ml bottle with integral pump dispenser," [retrieved on Mar. 25, 2011], retrieved from the internet: https://my.supplychain.nhs.uk/catalogue/product/mrb180/cleanser-alcohol-hand-rub-training-gel.

Technical bulletin, Surfonic L24-12 Surfactant. 1994.

International Search Report, PCT/US2010/049319, mailed Jun. 1, 2011.

International Search Report, PCT/US2010/049326, mailed Jun. 1, 2011.

International Search Report, PCT/US2010/049334, mailed Jun. 21, 2011.

International Search Report, PCT/US2010/049338, mailed Jun. 28, 2011.

* cited by examiner

CLEANING COMPOSITIONS AND EMULSIONS OR MICROEMULSIONS EMPLOYING EXTENDED CHAIN NONIONIC SURFACTANTS

CROSS-REFERENCE TO RELATED APPLICATIONS

This is a Continuation application of U.S. Ser. No. 12/884,638 filed Sep. 17, 2010, herein incorporated by reference in its entirety.

FIELD OF THE INVENTION

The invention relates to cleaning compositions and methods of use which employ synergistic combinations of linker co-surfactants and extended chain nonionic surfactants. Detergent compositions according to the invention are useful for removing a number of challenging stains such as those from non-trans fats and fatty acids through the formation of stable emulsions or microemulsions with such oily and greasy soils.

BACKGROUND OF THE INVENTION

Surfactants reduce the surface tension of water by adsorbing at the liquid-gas interface. They also reduce the interfacial tension between oil and water by adsorbing at the liquid-liquid interface. Surfactants are a primary component of most detergents. When dissolved in water, surfactants give a product the ability to remove dirt from surfaces. Each surfactant molecule has a hydrophilic head that is attracted to water molecules and a hydrophobic tail that repels water and simultaneously attaches itself to oil and grease in dirt. These opposing forces loosen the dirt and suspend it in the water.

Surfactants do the basic work of detergents and cleaning compositions by breaking up stains and keeping the dirt in the water solution to prevent re-deposition of the dirt onto the surface from which it has just been removed. Surfactants disperse dirt that normally does not dissolve in water.

Nonylphenol ethoxylates (NPEs) are predominantly used as industrial and domestic detergents as a surfactant. However, while effective, NPEs are disfavored due to environmental concerns. For example, NPEs are formed through the combination of ethylene oxide with nonylphenol (NP). Both NP and NPEs exhibit estrogen-like properties and may contaminate water, vegetation and marine life. NPE is also not readily biodegradable and remains in the environment or food chain for indefinite time periods.

An alternative to NPEs are alcohol ethoxylates (AEs). These alternatives are less toxic and degrade more quickly in the environment. However, it has recently been found that textiles washed with NPE free and phosphorous free detergents containing AEs smoke when exposed to high heat, e.g., in a steam tunnel in industrial laundry processes, or when ironed.

Surfactants are often incorporated into an oil-in-water microemulsion to make the products appear more homogenous. These cleaning products contain a variety of different surfactant systems in 5-20% solubilized oil which are then diluted with water prior to use. The surfactant systems generally employed in these cleaning products include a mixture of anionic or non-ionic surfactants and a short chain alcohol to help solubilize the oil phase and prevent liquid crystal formation. While short chain alcohols are effective, they also contribute to the volatile organic solvent content (VOC) of the product and pose flammability problems.

As can be seen there is a continuing need to develop effective, environmentally friendly, and safe surfactants and surfactant systems that can be used in cleaners of all kinds. This is particularly so in light of several new cleaning challenges that have emerged.

Health authorities have recently recommended that trans fats be reduced or eliminated in diets because they present health risks. In response, the food industry has largely replaced the use of trans fats with non-trans fats. These types of non-trans fats are the most difficult to remove from surfaces. The food industry has also experienced an unexplained higher frequency of laundry fires. Formulas and methods of cleaning to better remove non-trans fats, are prone to cause fire due their substantial heat of polymerization. Non-trans fats have conjugated double bonds that can polymerize and the substantial heat of polymerization involved can cause fire, for example, in a pile of rags used to mop up these non-trans fat soils.

As can be seen, there is a need in the industry for improvement of cleaning compositions, such as hard surface and laundry detergents and particularly the surfactants used therein so that difficult soils can be removed in a safe environmentally friendly and effective manner.

SUMMARY OF THE INVENTION

The invention meets the needs above by providing surfactant systems, mixtures or blends including extended chain nonionic surfactants in combination with linker co-surfactants. The mixtures form stable microemulsions with oils and fatty acids which can be the resultant product, such as lubricants, sunscreens, or triglyceride based products. According to the invention these emulsions or microemulsions are stable, irreversible, and can be created at low temperature, for example, room temperature.

In another embodiment the surfactant system or mixture can be used in a cleaning composition to emulsify and precipitate oils and greasy soils, such as non-trans fats and fatty acids. The surfactant system can be used alone as a pretreatment, or as a part of a cleaning composition such as a laundry detergent, hard surface cleaner or other emulsion or microemulsion.

The invention has many uses and applications, which include but are not limited to laundry cleaning, reduction of laundry fires due to non-trans fats, hard surface cleaning such as manual pot-n-pan cleaning, machine warewashing, all purpose cleaning, floor cleaning, CIP cleaning, open facility cleaning, foam cleaning, vehicle cleaning, etc. The invention is also relevant to non-cleaning related uses and applications such as dry lubes, tire dressings, polishes, etc. as well as triglyceride based lotions, suntan lotions, potentially pharmaceutical emulsions and microemulsions.

The surfactant mixture of the invention includes a synergistic combination of one or more extended chain nonionic surfactants combined with one or more linker co-surfactants. The linker so-surfactants comprise mono- and di-glycerides and/or fatty acid and fatty diacids. This system is highly effective at creating microemulsions with fatty acids and non-trans fats at relatively low temperatures. This system can be used in formulations for laundry detergents, hard surface cleaners, whether alkali or acid based or even by itself as a pre-spotting/pre-soaking agent.

In a further aspect of the present invention, a laundry detergent composition is provided which includes the surfactant system of the invention, and other detergent components such as builders, enzymes and the like. The laundry detergent product being adapted according to the invention to readily dissolve and disperse non-trans fats in commercial, industrial and personal laundry washing processes or in a pre-spotting treatment.

These and other objects, features and attendant advantages of the present invention will become apparent to those skilled in the art from a reading of the following detailed description of the preferred embodiment and the appended claims.

DETAILED DESCRIPTION OF THE INVENTION

Figure 1:
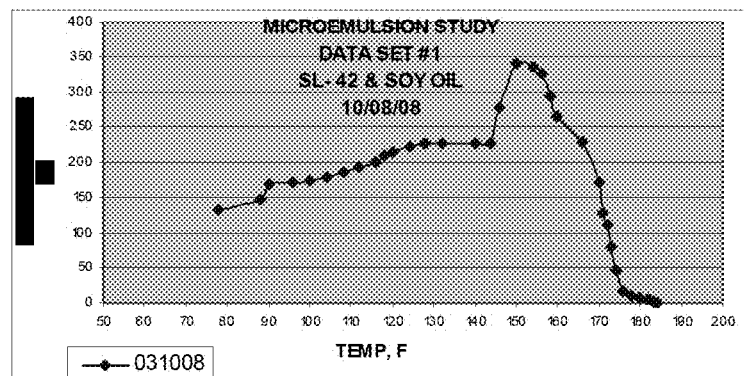
FIG. 1 is a graph that corresponds to the data presented in Table 6 and shows the micoremulsion study results.
Figure 2:
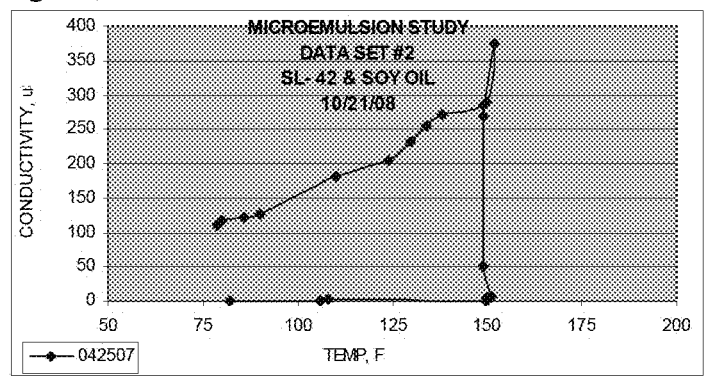
FIGS. 2 and 3 are graphs corresponding to data in table 7 of the microemulsion study showing conductivity over temperature (FIG. 2) and time (FIG. 3).
Figure 3:
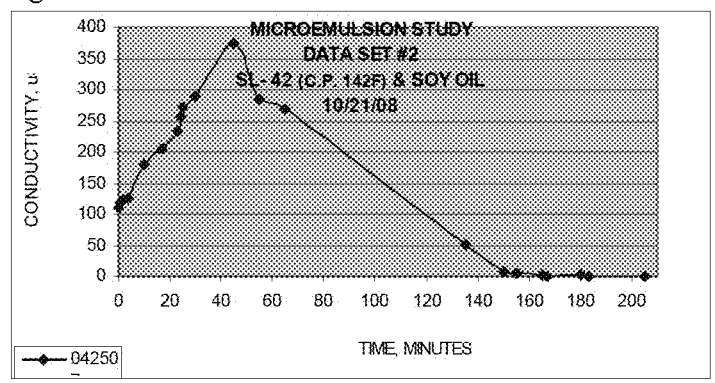
Figure 4:
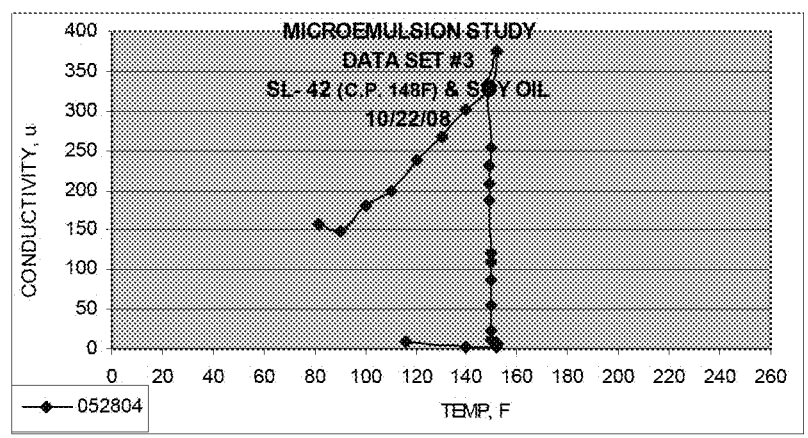
FIGS. 4 and 5 correspond to the data presented in table 8 of the microemulsion study showing conductivity over temperature (FIG. 4) and time (FIG. 5).
Figure 5:
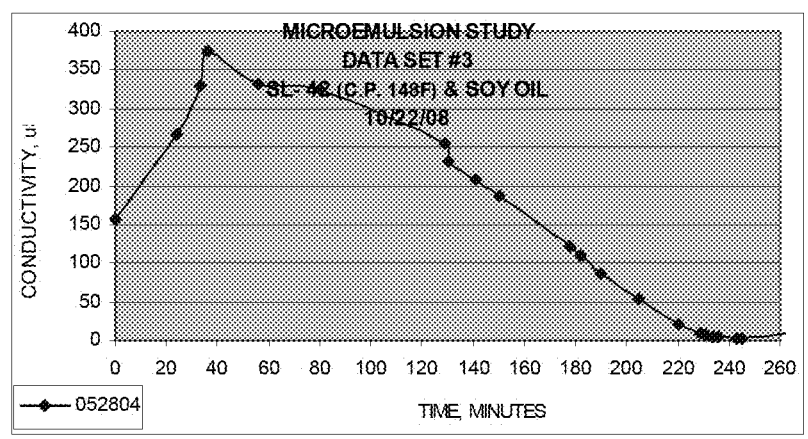
Figure 6:
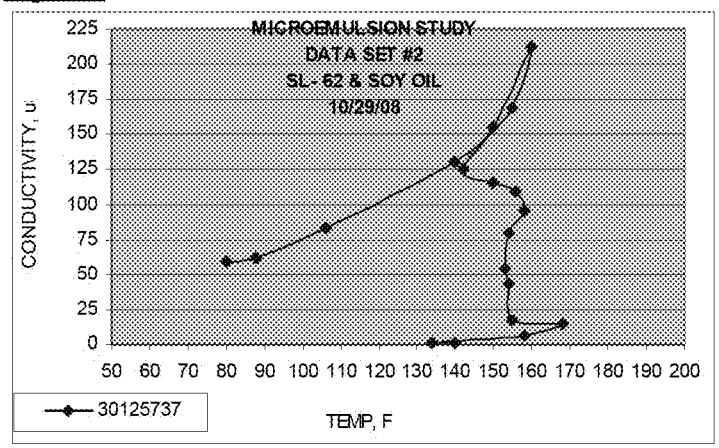
FIGS. 6 and 7 show the data from table 9 of the microemlusion study showing conductivity over temperature (FIG. 6) and time (FIG. 7).
Figure 7:
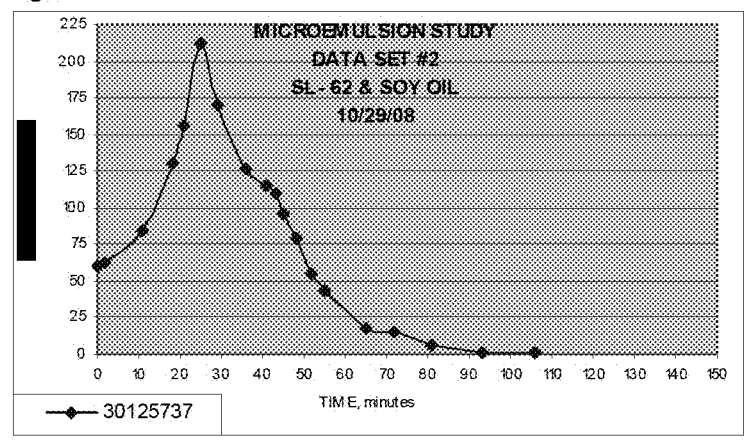

So that the invention maybe more readily understood, certain terms are first defined and certain test methods are described.

As used herein, "weight percent", "wt-%", "percent by weight", "% by weight", and variations thereof refer to the concentration of a substance as the weight of that substance divided by the total weight of the composition and multiplied by 100. It is understood that, as used here, "percent", "%", and the like are intended to be synonymous with "weight percent", "wt-%", etc.

As used herein, the term "about" refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "surfactant" as used herein is a compound that contains a lipophilic segment and a hydrophilic segment, which when added to water or solvents, reduces the surface tension of the system.

An "extended chain surfactant" is a surfactant having an intermediate polarity linking chain, such as a block of poly-propylene oxide, or a block of poly-ethylene oxide, or a block of poly-butylene oxide or a mixture thereof inserted between the surfactant's conventional lipophilic segment and hydrophilic segment.

The term "electrolyte" refers to a substance that will provide ionic conductivity when dissolved in water or when in contact with it; such compounds may either be solid or liquid.

As used herein, the term "microemulsion" refers to thermodynamically stable, isotropic dispersions consisting of nanometer size domains of water and/or oil stabilized by an interfacial film of surface active agent characterized by ultra low interfacial tension.

It should be noted that, as used in this specification and the appended claims, the singular forms "a," "an," and "the" include plural referents unless the content clearly dictates otherwise. Thus, for example, reference to a composition containing "a compound" includes a composition having two or more compounds. It should also be noted that the term "or" is generally employed in its sense including "and/or" unless the content clearly dictates otherwise.

The term "hard surface" refers to a solid, substantially non-flexible surface such as a counter top, tile, floor, wall, panel, window, plumbing fixture, kitchen and bathroom furniture, appliance, engine, circuit board, and dish.

The term "soft surface" refers to a softer, highly flexible material such as fabric, carpet, hair, and skin.

As used herein, the term "cleaning" refers to a method used to facilitate or aid in soil removal, bleaching, microbial population reduction, and any combination thereof.

"Soil" or "stain" refers to a non-polar oily substance which may or may not contain particulate matter such as mineral clays, sand, natural mineral matter, carbon black, graphite, kaolin, environmental dust, etc.

As used herein, the term "cleaning composition" includes, unless otherwise indicated, detergent compositions, laundry cleaning compositions, hard surface cleaning compositions, and personal care cleaning compositions for use in the health and beauty area. Cleaning compositions include granular, powder, liquid, gel, paste, bar form and/or flake type cleaning agents, laundry detergent cleaning agents, laundry soak or spray treatments, fabric treatment compositions, dish washing detergents and soaps, shampoos, body washes and soaps, and other similar cleaning compositions. As used herein, the term "fabric treatment composition" includes, unless otherwise indicated, fabric softening compositions, fabric enhancing compositions, fabric freshening compositions and combinations there of. Such compositions may be, but need not be rinse added compositions.

The term "laundry" refers to items or articles that are cleaned in a laundry washing machine. In general, laundry refers to any item or article made from or including textile materials, woven fabrics, non-woven fabrics, and knitted fabrics. The textile materials can include natural or synthetic fibers such as silk fibers, linen fibers, cotton fibers, polyester fibers, polyamide fibers such as nylon, acrylic fibers, acetate fibers, and blends thereof including cotton and polyester blends. The fibers can be treated or untreated.

Exemplary treated fibers include those treated for flame retardancy. It should be understood that the term "linen" is often used to describe certain types of laundry items including bed sheets, pillow cases, towels, table linen, table cloth, bar mops and uniforms. The invention additionally provides a composition and method for treating non-laundry articles and surfaces including hard surfaces such as dishes, glasses, and other ware.

Surfactant Systems Employing Nonionic Extended Chain Surfactants and Linker Co-Surfactants The surfactant system or mixture of the invention employs one or more extended chain surfactants. These are surfactants that have an intermediate polarity poly-propylene oxide chain (or linker) inserted between the lipophilic tail group and hydrophilic polar head, which may be anionic or nonionic.

Examples of lipophilic tails groups include hydrocarbons, alkyl ether, fluorocarbons or siloxanes. Examples of anionic and nonionic hydrophilic polar heads of the extended surfactant include, but are not necessarily limited to, groups such as polyoxyethylene sulfate, ethoxysulfate, carboxylate, ethoxycarboxylate, C6 sugar, xylitol, di-xylitol, ethoxy-xylitol, carboxylate and xytol, carboxylate and glucose.

Extended surfactants include a linker polypropylene glycol link.

The general formula for a nonionic extended surfactant is
$R\text{-}[L]_x\text{-}[O\text{—}CH_2\text{—}CH_2]_y$, Where R is the lipophilic moiety, a linear or branched, saturated or unsaturated, substituted or unsubstituted, aliphatic or aromatic hydrocarbon radical having from about 8 to 20 carbon atoms, L is a linking group, such as a block of poly-propylene oxide, a block of poly-ethylene oxide, a block of poly-butylene oxide or a mixture thereof; x is the chain length of the linking group ranging from 5-15; and y is the average degree of ethoxylation ranging from 1-5.

Anionic extended surfactants generally have the formula $R\text{-}[L]_x\text{-}[O\text{—}CH_2\text{—}CH_2]_y\text{—}M$ Where M is any ionic species such as carboxylates, sulfonates, sulfates, and phosphates. A cationic species will generally also be present for charge neutrality such as hydrogen, an alkali metal, alkaline earth metal, ammonium and ammonium ions which may be substituted with one or more organic groups These extended chain surfactants attain low tension and/or high solubilization in a single phase microemulsion with oils, such as non-trans fats with additional beneficial properties including, but not necessarily limited to, insensitivity to temperature and irreversibility. For example, in one embodiment the emulsions or microemulsions may function over a relatively wide temperature range of from about 20 to about 280° C., alternatively from about 20 to about 180° C. (350° F.).

Many extended chain anionic and nonionic surfactants are commercially available from a number of sources. Table 1 is a representative, nonlimiting listing of several examples of the same.

TABLE 1

| Extended Surfactants | Source | % Active | Structure |
|---|---|---|---|
| Plurafac SL-42(nonionic) | BASF | 100 | $C_{6\text{-}10}\text{—}(PO)_3(EO)_6$ |
| Plurafac SL-62(nonionic) | BASF | 100 | $C_{6\text{-}10}\text{—}(PO)_3(EO)_8$ |
| Lutensol XL-40(nonionic) | BASF | 100 | $C_{10}\text{—}(PO)_a(EO)_b$ |
| Lutensol XL-50(nonionic) | BASF | 100 | series, where a |
| Lutensol XL-60(nonionic) | BASF | 100 | is 1.0 to 1.5, |
| Lutensol XL-70(nonionic) | BASF | 100 | and b is 4 to 14. |
| Lutensol XL-79(nonionic) | BASF | 85 | |
| Lutensol XL-80(nonionic) | BASF | 100 | |
| Lutensol XL-89(nonionic) | BASF | 80 | |
| Lutensol XL-90(nonionic) | BASF | 100 | |
| Lutensol XL-99(nonionic) | BASF | 80 | |
| Lutensol XL-100(nonionic) | BASF | 100 | |
| Lutensol XL-140(nonionic) | BASF | 100 | |
| Ecosurf EH-3(nonionic) | Dow | 100 | 2-Ethyl Hexyl |
| Ecosurf EH-6(nonionic) | Dow | 100 | $(PO)_m(EO)_n$ |
| Ecosurf EH-9(nonionic) | Dow | 100 | series |
| Ecosurf SA-4(nonionic) | Dow | 100 | $C_{6\text{-}12}(PO)_{3\text{-}4}(EO)_4$ |
| Ecosurf SA-7(nonionic) | Dow | 100 | $C_{6\text{-}12}(PO)_{3\text{-}4}(EO)_7$ |
| Ecosurf SA-9(nonionic) | Dow | 100 | $C_{6\text{-}12}(PO)_{3\text{-}4}(EO)_9$ |
| Surfonic PEA-25(nonionic) | Huntsman | 100 | $C_{12\text{-}14}(PO)_2N[(EO)_{2.5}]_2$ |
| X-AES (anionic) | Huntsman | 23 | $C_{12\text{-}14}\text{—}(PO)_{16}\text{-}(EO)_2\text{-}$sulfate |

TABLE 1-continued

| Extended Surfactants | Source | % Active | Structure |
|---|---|---|---|
| X-LAE (nonionic) | Huntsman | 100 | $C_{12\text{-}14}\text{—}(PO)_{16}(EO)_{12}$ |
| Alfoterra 123-4S(anionic) | Sasol | 30 | $C_{12\text{-}13}\text{—}(PO)_4\text{-sulfate}$ |
| Alfoterra 123-8S(anionic) | Sasol | 30 | $C_{12\text{-}13}\text{—}(PO)_8\text{-sulfate}$ |
| Marlowet 4561 (nonionic under acidic condition, anionic under alkaline condition) | Sasol | 90 | $C_{16\text{-}18}(PO)_4(EO)_5\text{-}$carboxylic acid |
| Marlowet 4560 (nonionic under acidic condition, anionic under alkaline condition) | Sasol | 90 | $C_{16\text{-}18}(PO)_4(EO)_2\text{-}$carboxylic acid |
| Marlowet 4539 (nonionic under acidic condition, anionic under alkaline condition) | Sasol | 90 | Iso $C_9\text{—}(PO)_2EO_2\text{-}$carboxylic acid |

According to the invention, a nonionic extended chain surfactant is employed in synergistic combination with a second linker co-surfactant. The linker co-surfactant is an additive which "sticks to" or "associates with" the extended chain nonionic surfactant and links it with the molecules in the bulk phase, and hence increase the "reach" of the surfactant molecules which are adsorbed at interface, thus enhancing their performance. Linker co-surfactants which may be used according to the invention include mono- and di-glycerides, and/or fatty acids and fatty diacids. Suitable fatty acids are saturated and/or unsaturated and can be obtained from natural sources such a plant or animal esters (e.g., palm kernel oil, palm oil, coconut oil, babassu oil, safflower oil, tall oil, tallow and fish oils, grease, and mixtures thereof), or synthetically prepared (e.g., via the oxidation of petroleum or by hydrogenation of carbon monoxide via the Fisher Tropsch process). Useful fatty acids are saturated $C_{12}$ fatty acid, saturated $C_{12\text{-}14}$ fatty acids, saturated or unsaturated $C_{12\text{-}18}$ fatty acids, and a mixture thereof. Examples of suitable saturated fatty acids include: captic, lauric, myristic, palmitic, stearic, arachidic and behenic acid. Suitable unsaturated fatty acids include: palmitoleic, oleic, linoleic, linolenic and ricinoleic acid.

Suitable fatty diacids include Diabolic acid (15,16-dimethyltriacontanedioic acid) (13,14-dimethyloctacosanedioic acid) (15,16-dimethyltriacontanedioic acid) and other Biphytanic diacids.

Linker surfactants with a balanced cross sectional area are also beneficial. While not wishing to be bound by any theory, applicants postulate that the beneficial use of surfactants with a balanced cross-sectional area, for example surfactants with a small hydrophilic head and/or surfactants with twin or bulky hydrophobic tail(s) help the overall packing at the water and oil interface towards a more planar interface. Other possible linkers with balanced cross sectional areas include branched alcohol ethoxylates and Guerbet alcohol ethoxylates.

According to the invention, emulsions or microemulsions can be formed upon heating that are stable and irreversible, i.e. the emulsion or microemulsion does not revert as it cools down. In this embodiment, the surfactant system includes approximately 33 wt. % nonionic extended chain surfactant, 33 wt. % water and 33 wt. % oil (or fatty acid co-surfactant).

In a cleaning composition or soil removal and treatment, the ratio of nonionic extended surfactant to fatty acid co-surfactant is approximately 2:1. When a mono or diglyceride is used the ratio is approximately 7:1 of nonionic extended surfactant to mono or diglyceride.

The surfactant system of the invention is capable of forming emulsions or microemulsions with, or in cleaning compositions for removing or treated stains caused by oils and fatty acids including hydrocarbon type oils, vegetable oils, organic oils, mineral oils, synthetic oils, petrochemical oils, volatile essential oils, including fatty acids, lipids as well as triglycerides.

This feature may be used for removal of the oils in cleaning products or in any other product which requires an oil emulsion or microemulsion such as lubricants, suntan lotions, pharmaceutical applications hair products such as shampoos, gels, conditioners and the like, Petroleum products such as diesel fuel (petrodiesel), ethane (and other short-chain alkanes), fuel oils (heaviest of commercial fuels, used in ships/furnaces), gasoline (petrol), jet fuel, kerosene, and liquefied petroleum gas, Lubrication products for various personal and engineering purposes, detergents, fertilizers, medicines, paints, plastics, synthetic fibers, and synthetic rubber.

Cleaning Compositions Comprising Extended Chain Surfactants

The surfactant system of the invention may be used alone, as a pre-treatment, pre-soak or pre-spot composition in combination with a traditional detergent or cleaner, or may be incorporated within a cleaning composition. The invention comprises both hard surface and soft surface cleaning compositions including the disclosed surfactant system.

In one embodiment, the invention employs the surfactant system of the invention, an acid source, a solvent, a water conditioning agent, and water to make a hard surface cleaner which will be effective at removing greasy and oily soils from surfaces such as showers, sinks, toilets, bathtubs, countertops, windows, minors, transportation vehicles, floors, and the like. These surfaces can be those typified as "hard surfaces" (such as walls, floors, bed-pans).

A typical hard surface formulation at about 18% activity includes between about 40 wt. % and about 80 wt. % surfactant system of the invention, between about 3 wt. % and about 18 wt. % water conditioning agent, between about 0.1 wt. % and about 0.55 wt. % acid source, between about 0 wt % and about 10 wt. % solvent and between about 10 wt. % and about 60 wt. % water.

Particularly, the cleaning compositions include between about 45 wt. % and about 75 wt. % surfactant system of the invention, between about 0 wt. % and about 10 wt. % optional co-surfactant, between about 5 wt. % and about 15 wt. % water conditioning agent, between about 0.3 wt. % and about 0.5 wt. % acid source, between about 0 and about 6 wt. % solvent and between about 15 wt. % and about 50 wt. % water. In other embodiments, similar intermediate concentrations and use concentrations may also be present in the cleaning compositions of the invention.

In a laundry detergent formulation the compositions of the invention typically include the surfactant system of the invention, and a builder, optionally with an enzyme. Examples of such standard laundry detergent ingredients, which are well known to those skilled in the art, are provided in the following paragraphs.

Additional Components

While not essential for the purposes of the present invention, the non-limiting list of additional components illustrated hereinafter are suitable for use in the instant compositions and may be desirably incorporated in certain embodiments of the invention, for example to assist or enhance cleaning performance, for treatment of the substrate to be cleaned, or to modify the aesthetics of the cleaning composition as is the case with perfumes, colorants, dyes or the like. The precise nature of these additional components, and levels of incorporation thereof, will depend on the physical form of the composition and the nature of the cleaning operation for which it is to be used. Suitable additional materials include, but are not limited to, surfactants, builders, chelating agents, dye transfer inhibiting agents, viscosity modifiers, dispersants, additional enzymes, and enzyme stabilizers, catalytic materials, bleaches, bleach activators, hydrogen peroxide, sources of hydrogen peroxide, preformed peracids, polymeric dispersing agents, threshold inhibitors for hard water precipitation pigments, clay soil removal/anti-redeposition agents, brighteners, suds suppressors, dyes, fabric hueing agents, perfumes, structure elasticizing agents, fabric softeners, carriers, hydrotropes, processing aids, solvents, pigments antimicrobials, pH buffers, processing aids, active fluorescent whitening ingredient, additional surfactants and mixtures thereof. In addition to the disclosure below, suitable examples of such other adjuncts and levels of use are found in U.S. Pat. Nos. 5,576,282, 6,306,812 B1 and 6,326,348 B1 that are incorporated by reference.

As stated, the adjunct ingredients are not essential to Applicants' compositions. Thus, certain embodiments of Applicants' compositions do not contain additional materials. However, when one or more additional materials are present, such one or more additional components may be present as detailed below:

The liquid detergent herein has a neat pH of from about 7 to about 13, or about 7 to about 9, or from about 7.2 to about 8.5, or from about 7.4 to about 8.2. The detergent may contain a buffer and/or a pH-adjusting agent, including inorganic and/or organic alkalinity sources and acidifying agents such as water-soluble alkali metal, and/or alkali earth metal salts of hydroxides, oxides, carbonates, bicarbonates, borates, silicates, phosphates, and/or metasilicates; or sodium hydroxide, potassium hydroxide, pyrophosphate, orthophosphate, polyphosphate, and/or phosphonate. The organic alkalinity source herein includes a primary, secondary, and/or tertiary amine. The inorganic acidifying agent herein includes HF, HCl, HBr, HI, boric acid, sulfuric acid, phosphoric acid, and/or sulphonic acid; or boric acid. The organic acidifying agent herein includes substituted and substituted, branched, linear and/or cyclic $C_{1-30}$ carboxylic acid.

Bleaching Agents—

The cleaning compositions of the present invention may comprise one or more bleaching agents. Suitable bleaching agents other than bleaching catalysts include photobleaches, bleach activators, hydrogen peroxide, sources of hydrogen peroxide, pre-formed peracids and mixtures thereof. In general, when a bleaching agent is used, the compositions of the present invention may comprise from about 0.1% to about 50% or even from about 0.1% to about 25% bleaching agent by weight of the subject cleaning composition. Examples of suitable bleaching agents include:

(1) preformed peracids: Suitable preformed peracids include, but are not limited to, compounds selected from the group consisting of percarboxylic acids and salts, percarbonic acids and salts, perimidic acids and salts, peroxymonosulfuric acids and salts, for example, Oxzone®, and mixtures thereof. Suitable percarboxylic acids include hydrophobic and hydrophilic peracids having the formula R—(C—O)O—O-M wherein R is an alkyl group, optionally branched, having, when the peracid is hydrophobic, from 6 to 14 carbon atoms, or from 8 to 12 carbon atoms and, when the peracid is hydrophilic, less than 6 carbon atoms or even less than 4 carbon atoms; and M is a counterion, for example, sodium, potassium or hydrogen; (2) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. When employed, inorganic perhydrate salts are typically present in amounts of from 0.05 to 40 wt %, or 1 to 30 wt % of the overall composition and are typically incorporated into such compositions as a crystalline solid that may be coated. Suitable coatings include, inorganic salts such as alkali metal silicate, carbonate or borate salts or mixtures thereof, or organic materials such as water-soluble or dispersible polymers, waxes, oils or fatty soaps; and(3) bleach activators having R—(C—O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). Suitable bleach activators are also disclosed in WO 98/17767. While any suitable bleach activator may be employed, in one aspect of the invention the subject cleaning composition may comprise NOBS, TAED or mixtures thereof.

When present, the peracid and/or bleach activator is generally present in the composition in an amount of from about 0.1 to about 60 wt %, from about 0.5 to about 40 wt % or even from about 0.6 to about 10 wt % based on the composition. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or even 2:1 to 10:1.

Additional Surfactant

In some embodiments, the compositions of the invention include an additional surfactant. Additional surfactants can be anionic, nonionic, cationic zwitterionic and can also include additional extended chain surfactant as discussed herein.

The cleaning composition can contain an additional anionic surfactant component that includes a detersive amount of an anionic surfactant or a mixture of anionic surfactants. Anionic surfactants are desirable in cleaning compositions because of their wetting and detersive properties. The anionic surfactants that can be used according to the invention include any anionic surfactant available in the cleaning industry. Suitable groups of anionic surfactants include sulfonates and sulfates. Suitable surfactants that can be provided in the anionic surfactant component include alkyl aryl sulfonates, secondary alkane sulfonates, alkyl methyl ester sulfonates, alpha olefin sulfonates, alkyl ether sulfates, alkyl sulfates, and alcohol sulfates.

Suitable alkyl aryl sulfonates that can be used in the cleaning composition can have an alkyl group that contains 6 to 24 carbon atoms and the aryl group can be at least one of benzene, toluene, and xylene. A suitable alkyl aryl sulfonate includes linear alkyl benzene sulfonate. A suitable linear alkyl benzene sulfonate includes linear dodecyl benzyl sulfonate that can be provided as an acid that is neutralized to form the sulfonate. Additional suitable alkyl aryl sulfonates include xylene sulfonate and cumene sulfonate.

Suitable alkane sulfonates that can be used in the cleaning composition can have an alkane group having 6 to 24 carbon atoms. Suitable alkane sulfonates that can be used include secondary alkane sulfonates. A suitable secondary alkane sulfonate includes sodium $C_{14}$-$C_{17}$ secondary alkyl sulfonate commercially available as Hostapur SAS from Clariant.

Suitable alkyl methyl ester sulfonates that can be used in the cleaning composition include those having an alkyl group containing 6 to 24 carbon atoms. Suitable alpha olefin sulfonates that can be used in the cleaning composition include those having alpha olefin groups containing 6 to 24 carbon atoms.

Suitable alkyl ether sulfates that can be used in the cleaning composition include those having between about 1 and about 10 repeating alkoxy groups, between about 1 and about 5 repeating alkoxy groups. In general, the alkoxy group will contain between about 2 and about 4 carbon atoms. A suitable alkoxy group is ethoxy. A suitable alkyl ether sulfate is sodium lauryl ether sulfate and is available under the name Steol CS-460.

Suitable alkyl sulfates that can be used in the cleaning composition include those having an alkyl group containing 6 to 24 carbon atoms. Suitable alkyl sulfates include, but are not limited to, sodium lauryl sulfate and sodium lauryl/myristyl sulfate.

Suitable alcohol sulfates that can be used in the cleaning composition include those having an alcohol group containing about 6 to about 24 carbon atoms.

The anionic surfactant can be neutralized with an alkaline metal salt, an amine, or a mixture thereof. Suitable alkaline metal salts include sodium, potassium, and magnesium. Suitable amines include monoethanolamine, triethanolamine, and monoisopropanolamine. If a mixture of salts is used, a suitable mixture of alkaline metal salt can be sodium and magnesium, and the molar ratio of sodium to magnesium can be between about 3:1 and about 1:1.

The cleaning composition, when provided as a concentrate, can include the additional anionic surfactant component in an amount sufficient to provide a use composition having desired wetting and detersive properties after dilution with water. The concentrate can contain about 0.1 wt. % to about 0.5 wt. %, about 0.1 wt. % to about 1.0 wt. %, about 1.0 wt. % to about 5 wt. %, about 5 wt. % to about 10 wt. %, about 10 wt. % to about 20 wt. %, 30 wt. %, about 0.5 wt. % to about 25 wt. %, and about 1 wt. % to about 15 wt. %, and similar intermediate concentrations of the anionic surfactant.

The cleaning composition can contain a nonionic surfactant component that includes a detersive amount of nonionic surfactant or a mixture of nonionic surfactants. Nonionic surfactants can be included in the cleaning composition to enhance grease removal properties. Although the surfactant component can include a nonionic surfactant component, it should be understood that the nonionic surfactant component can be excluded from the detergent composition.

Additional nonionic surfactants that can be used in the composition include polyalkylene oxide surfactants (also known as polyoxyalkylene surfactants or polyalkylene glycol surfactants). Suitable polyalkylene oxide surfactants include polyoxypropylene surfactants and polyoxyethylene glycol surfactants. Suitable surfactants of this type are synthetic organic polyoxypropylene (PO)-polyoxyethylene (EO) block copolymers. These surfactants include a di-block polymer comprising an EO block and a PO block, a center block of polyoxypropylene units (PO), and having blocks of polyoxyethylene grafted onto the polyoxypropylene unit or a center block of EO with attached PO blocks. Further, this surfactant can have further blocks of either polyoxyethylene or polyoxypropylene in the molecules. A suitable average molecular weight range of useful surfactants can be about 1,000 to about 40,000 and the weight percent content of ethylene oxide can be about 10-80 wt %.

Other nonionic surfactants include alcohol alkoxylates. An suitable alcohol alkoxylate include linear alcohol ethoxylates such as Tomadol™ 1-5 which is a surfactant containing an alkyl group having 11 carbon atoms and 5 moles of ethylene oxide. Additional alcohol alkoxylates include alkylphenol ethoxylates, branched alcohol ethoxylates, secondary alcohol ethoxylates (e.g., Tergitol 15-S-7 from Dow Chemical), castor oil ethoxylates, alkylamine ethoxylates, tallow amine ethoxylates, fatty acid ethoxylates, sorbital oleate ethoxylates, end-capped ethoxylates, or mixtures thereof. Additional nonionic surfactants include amides such as fatty alkanolamides, alkyldiethanolamides, coconut diethanolamide, lauric diethanolamide, polyethylene glycol cocoamide (e.g., PEG-6 cocoamide), oleic diethanolamide, or mixtures thereof. Additional suitable nonionic surfactants include polyalkoxylated aliphatic base, polyalkoxylated amide, glycol esters, glycerol esters, amine oxides, phosphate esters, alcohol phosphate, fatty triglycerides, fatty triglyceride esters, alkyl ether phosphate, alkyl esters, alkyl phenol ethoxylate phosphate esters, alkyl polysaccharides, block copolymers, alkyl polyglucosides, or mixtures thereof.

When nonionic surfactants are included in the detergent composition concentrate, they can be included in an amount of at least about 0.1 wt. % and can be included in an amount of up to about 15 wt. %. The concentrate can include about 0.1 to 1.0 wt. %, about 0.5 wt. % to about 12 wt. % or about 2 wt. % to about 10 wt. % of the nonionic surfactant.

Amphoteric surfactants can also be used to provide desired detersive properties. Suitable amphoteric surfactants that can be used include, but are not limited to: betaines, imidazolines, and propionates. Suitable amphoteric surfactants include, but are not limited to: sultaines, amphopropionates, amphodipropionates, aminopropionates, aminodipropionates, amphoacetates, amphodiacetates, and amphohydroxypropylsulfonates.

When the detergent composition includes an amphoteric surfactant, the amphoteric surfactant can be included in an amount of about 0.1 wt % to about 15 wt %. The concentrate can include about 0.1 wt % to about 1.0 wt %, 0.5 wt % to about 12 wt % or about 2 wt % to about 10 wt % of the amphoteric surfactant.

The cleaning composition can contain a cationic surfactant component that includes a detersive amount of cationic surfactant or a mixture of cationic surfactants. Cationic co-surfactants that can be used in the cleaning composition include, but are not limited to: amines such as primary, secondary and tertiary monoamines with $C_{18}$ alkyl or alkenyl chains, ethoxylated alkylamines, alkoxylates of ethylenediamine, imidazoles such as a 1-(2-hydroxyethyl)-2-imidazoline, a 2-alkyl-1-(2-hydroxyethyl)-2-imidazoline, and the like; and quaternary ammonium salts, as for example, alkylquaternary ammonium chloride surfactants such as n-alkyl($C_{12}$-$C_{18}$) dimethylbenzyl ammonium chloride, n-tetradecyldimethylbenzylammonium chloride monohydrate, and a naphthylene-substituted quaternary ammonium chloride such as dimethyl-1-naphthylmethylammonium chloride.

Builders—The cleaning compositions of the present invention may comprise one or more detergent builders or builder systems. When a builder is used, the subject composition will typically comprise at least about 1%, from about 5% to about 60%, or even from about 10% to about 40% builder by weight of the subject composition. The detergent may contain an inorganic or organic detergent builder which counteracts the effects of calcium, or other ion, water hardness. Examples include the alkali metal citrates, succinates, malonates, carboxymethyl succinates, carboxylates, polycarboxylates and polyacetyl carboxylate; or sodium, potassium and lithium salts of oxydisuccinic acid, mellitic acid, benzene polycarboxylic acids, and citric acid; or citric acid and citrate salts. Organic phosphonate type sequestering agents such as DEQUEST® by Monsanto and alkanehydroxy phosphonates are useful. Other organic builders include higher molecular weight polymers and copolymers, e.g., polyacrylic acid, polymaleic acid, and polyacrylic/polymaleic acid copolymers and their salts, such as SOKALAN® by BASF. Generally, the builder may be up to 30%, or from about 1% to about 20%, or from abut 3% to about 10%.

The compositions may also contain from about 0.01% to about 10%, or from about 2% to about 7%, or from about 3% to about 5% of a $C_{8-20}$ fatty acid as a builder. The fatty acid can also contain from about 1 to about 10 EO units. Suitable fatty acids are saturated and/or unsaturated and can be obtained from natural sources such a plant or animal esters (e.g., palm kernel oil, palm oil, coconut oil, babassu oil, safflower oil, tall oil, tallow and fish oils, grease, and mixtures thereof), or synthetically prepared (e.g., via the oxidation of petroleum or by hydrogenation of carbon monoxide via the Fisher Tropsch process). Useful fatty acids are saturated $C_{12}$ fatty acid, saturated $C_{12-14}$ fatty acids, saturated or unsaturated $C_{12-18}$ fatty acids, and a mixture thereof. Examples of suitable saturated fatty acids include captic, lauric, myristic, palmitic, stearic, arachidic and behenic acid. Suitable unsaturated fatty acids include: palmitoleic, oleic, linoleic, linolenic and ricinoleic acid.

Chelating Agents—The cleaning compositions herein may contain a chelating agent. Suitable chelating agents include copper, iron and/or manganese chelating agents and mixtures thereof. When a chelating agent is used, the subject composition may comprise from about 0.005% to about 15% or even from about 3.0% to about 10% chelating agent by weight of the subject composition.

Dye Transfer Inhibiting Agents—The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Optical Brightener

In some embodiments, an optical brightener component, may be present in the compositions of the present invention. The optical brightener can include any brightener that is capable of eliminating graying and yellowing of fabrics. Typically, these substances attach to the fibers and bring about a brightening and simulated bleaching action by converting invisible ultraviolet radiation into visible longer-wavelength light, the ultraviolet light absorbed from sunlight being irradiated as a pale bluish fluorescence and, together with the yellow shade of the grayed or yellowed laundry, producing pure white.

Fluorescent compounds belonging to the optical brightener family are typically aromatic or aromatic heterocyclic materials often containing condensed ring systems. An important feature of these compounds is the presence of an uninterrupted chain of conjugated double bonds associated with an aromatic ring. The number of such conjugated double bonds is dependent on substituents as well as the planarity of the fluorescent part of the molecule. Most brightener compounds are derivatives of stilbene or 4,4'-diamino stilbene, biphenyl, five membered heterocycles (triazoles, oxazoles, imidazoles, etc.) or six membered heterocycles (cumarins, naphthalamides, triazines, etc.).

Optical brighteners useful in the present invention are known and commercially available. Commercial optical brighteners which may be useful in the present invention can be classified into subgroups, which include, but are not necessarily limited to, derivatives of stilbene, pyrazoline, coumarin, carboxylic acid, methinecyanines, dibenzothiophene-5,5-dioxide, azoles, 5- and 6-membered-ring heterocycles and other miscellaneous agents. Examples of these types of brighteners are disclosed in "The Production and Application of Fluorescent Brightening Agents", M. Zahradnik, Published by John Wiley & Sons, New York (1982), the disclosure of which is incorporated herein by reference.

Stilbene derivatives which may be useful in the present invention include, but are not necessarily limited to, derivatives of bis(triazinyl)amino-stilbene; bisacylamino derivatives of stilbene; triazole derivatives of stilbene; oxadiazole derivatives of stilbene; oxazole derivatives of stilbene; and styryl derivatives of stilbene. In an embodiment, optical brighteners include stilbene derivatives.

In some embodiments, the optical brightener includes Tinopal UNPA, which is commercially available through the Ciba Geigy Corporation located in Switzerland.

Additional optical brighteners for use in the present invention include, but are not limited to, the classes of substance of 4,4'-diamino-2,2'-stilbenedisulfonic acids (flavonic acids), 4,4'-distyrylbiphenyls, methylumbelliferones, coumarins, dihydroquinolinones, 1,3-diarylpyrazolines, naphthalimides, benzoxazol, benzisoxazol and benzimidazol systems, and pyrene derivatives substituted by heterocycles, and the like. Suitable optical brightener levels include lower levels of from about 0.01, from about 0.05, from about 0.1 or even from about 0.2 wt % to upper levels of 0.5 or even 0.75 wt %.

Dispersants—The compositions of the present invention can also contain dispersants. Suitable water-soluble organic materials include the homo- or co-polymeric acids or their salts, in which the polycarboxylic acid comprises at least two carboxyl radicals separated from each other by not more than two carbon atoms.

Additional Enzymes—The cleaning compositions can comprise one or more enzymes which provide cleaning performance and/or fabric care benefits. Enzymes can be included herein for a wide variety of fabric laundering purposes, including removal of protein-based, carbohydrate-based, or triglyceride-based stains, for example, and/or for fabric restoration. Examples of suitable enzymes include, but are not limited to, hemicellulases, peroxidases, proteases, cellulases, xylanases, lipases, phospholipases, esterases, cutinases, pectinases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, amylases, or combinations thereof and may be of any suitable origin. The choice of enzyme(s) takes into account factors such as pH-activity, stability optima, thermostability, stability versus active detergents, chelants, builders, etc. A detersive enzyme mixture useful herein is a protease, lipase, cutinase and/or cellulase in conjunction with amylase. Sample detersive enzymes are described in U.S. Pat. No. 6,579,839.

Enzymes are normally present at up to about 5 mg, more typically from about 0.01 mg to about 3 mg by weight of active enzyme per gram of the detergent. Stated another way, the detergent herein will typically contain from about 0.001% to about 5%, or from about 0.01% to about 2%, or from about 0.05% to about 1% by weight of a commercial enzyme preparation. Protease enzymes are present at from about 0.005 to about 0.1 AU of activity per gram of detergent. Proteases useful herein include those like subtilisins from *Bacillus* [e.g. *subtilis, lentus, licheniformis, amyloliquefaciens* (BPN, BPN'), alcalophilus,] e.g. Esperase®, Alcalase®, Everlase® and Savinase® (Novozymes), BLAP and variants (Henkel). Further proteases are described in EP 130756, WO 91/06637, WO 95/10591 and WO 99/20726.

Amylases are described in GB Pat. #1 296 839, WO 94/02597 and WO 96/23873; and available as Purafect Ox Am® (Genencor), Termamyl®, Natalase®, Ban®, Fungamyl®, Duramyl® (all Novozymes), and RAPIDASE (International Bio-Synthetics, Inc).

The cellulase herein includes bacterial and/or fungal cellulases with a pH optimum between 5 and 9.5. Suitable cellulases are disclosed in U.S. Pat. No. 4,435,307 to Barbesgoard, et al., issued Mar. 6, 1984. Cellulases useful herein include bacterial or fungal cellulases, e.g. produced by *Humicola insolens*, particularly DSM 1800, e.g. 50 kD and ~43 kD (Carezyyme®). Additional suitable cellulases are the EGIII cellulases from *Trichoderma longibrachiatum*. WO 02/099091 by Novozymes describes an enzyme exhibiting endo-beta-glucanase activity (EC 3.2.1.4) endogenous to *Bacillus* sp., DSM 12648; for use in detergent and textile applications; and an anti-redeposition endoglucanase in WO 04/053039. Kao's EP 265 832 describes alkaline cellulase K, CMCase I and CMCase II isolated from a culture product of *Bacillus* sp KSM-635. Kao further describes in EP 1 350 843 (KSM 5237; 1139; KSM 64; KSM N131), EP 265 832A (KSM 635, FERM BP 1485) and EP 0 271 044 A (KSM 534, FERM BP 1508; KSM 539, FERM BP 1509; KSM 577, FERM BP 1510; KSM 521, FERM BP 1507; KSM 580, FERM BP 1511; KSM 588, FERM BP 1513; KSM 597, FERM BP 1514; KSM 522, FERM BP 1512; KSM 3445, FERM BP 1506; KSM 425. FERM BP 1505) readily-mass producible and high activity alkaline cellulases/endo-glucanases for an alkaline environment. Such endoglucanase may contain a polypeptide (or variant thereof) endogenous to one of the above *Bacillus* species. Other suitable cellulases are Family 44 Glycosyl Hydrolase enzymes exhibiting endo-beta-1,4-glucanase activity from Paenibacilus polyxyma (wild-type) such as XYG1006 described in WO 01/062903 or variants thereof. Carbohydrases useful herein include e.g. mannanase (see, e.g., U.S. Pat. No. 6,060,299), pectate lyase (see, e.g., WO99/27083), cyclomaltodextrin glucanotransferase (see, e.g., WO96/33267), and/or xyloglucanase (see, e.g., WO99/02663). Bleaching enzymes useful herein with enhancers include e.g. peroxidases, laccases, oxygenases, lipoxygenase (see, e.g., WO 95/26393), and/or (non-heme) haloperoxidases.

Suitable endoglucanases include: 1) An enzyme exhibiting endo-beta-1,4-glucanase activity (E.C. 3.2.1.4), with a sequence at least 90%, or at least 94%, or at least 97% or at least 99%, or 100% identity to the amino acid sequence of positions 1-773 of SEQ ID NO:2 in WO 02/099091; or a fragment thereof that has endo-beta-1,4-glucanase activity. GAP in the GCG program determines identity using a GAP creation penalty of 3.0 and GAP extension penalty of 0.1. See WO 02/099091 by Novozymes A/S on Dec. 12, 2002, e.g., Celluclean™ by Novozymes A/S. GCG refers to sequence analysis software package (Accelrys, San Diego, Calif., USA). GCG includes a program called GAP which uses the Needleman and Wunsch algorithm to find the alignment of two complete sequences that maximizes the number of matches and minimizes the number of gaps; and 2) Alkaline endoglucanase enzymes described in EP 1 350 843A published by Kao on Oct. 8, 2003 ([0011]-[0039] and examples 1-4).

Suitable lipases include those produced by *Pseudomonas* and Chromobacter, and LIPOLASE®, LIPOLASE ULTRA®, LIPOPRIME® and LIPEX® from Novozymes. See also Japanese Patent Application 53-20487, laid open on Feb. 24, 1978, available from Areario Pharmaceutical Co. Ltd., Nagoya, Japan, under the trade name Lipase P "Amano". Other commercial lipases include Amano-CES, lipases ex *Chromobacter viscosum*, available from Toyo Jozo Co., Tagata, Japan; and *Chromobacter viscosum* lipases from U.S. Biochemical Corp., U.S.A. and Diosynth Co., The Netherlands, and lipases ex *Pseudomonas gladioli*. Also suitable are cutinases [EC 3.1.1.50] and esterases.

Enzymes useful for liquid detergent formulations, and their incorporation into such formulations, are disclosed in U.S. Pat. No. 4,261,868 to Hora, et al., issued Apr. 14, 1981. In an embodiment, the liquid composition herein is substantially free of (i.e. contains no measurable amount of) wild-type protease enzymes. A typical combination is an enzyme cocktail that may comprise, for example, a protease and lipase in conjunction with amylase. When present in a cleaning composition, the aforementioned additional enzymes may be present at levels from about 0.00001% to about 2%, from about 0.0001% to about 1% or even from about 0.001% to about 0.5% enzyme protein by weight of the composition.

Enzyme Stabilizers—Enzymes for use in detergents can be stabilized by various techniques. The enzymes employed herein can be stabilized by the presence of water-soluble sources of calcium and/or magnesium ions in the finished compositions that provide such ions to the enzymes. In case of aqueous compositions comprising protease, a reversible protease inhibitor, such as a boron compound, can be added to further improve stability.

A useful enzyme stabilizer system is a calcium and/or magnesium compound, boron compounds and substituted boric acids, aromatic borate esters, peptides and peptide derivatives, polyols, low molecular weight carboxylates, relatively hydrophobic organic compounds [e.g. certain esters, diakyl glycol ethers, alcohols or alcohol alkoxylates], alkyl ether carboxylate in addition to a calcium ion source, benzamidine hypochlorite, lower aliphatic alcohols and carboxylic acids, N,N-bis(carboxymethyl) serine salts; (meth)acrylic acid-(meth)acrylic acid ester copolymer and PEG; lignin compound, polyamide oligomer, glycolic acid or its salts; poly hexa methylene biguanide or N,N-bis-3-amino-propyl-dodecyl amine or salt; and mixtures thereof. The detergent may contain a reversible protease inhibitor e.g., peptide or protein type, or a modified subtilisin inhibitor of family VI and the plasminostrepin; leupeptin, peptide trifluoromethyl ketone, or a peptide aldehyde. Enzyme stabilizers are present from about 1 to about 30, or from about 2 to about 20, or from about 5 to about 15, or from about 8 to about 12, millimoles of stabilizer ions per liter.

Catalytic Metal Complexes—Applicants' cleaning compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediamine-tetra(methylenephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282. Cobalt bleach catalysts useful herein are known, and are described, for example, in U.S. Pat. Nos. 5,597,936; 5,595,967. Such cobalt catalysts are readily prepared by known procedures, such as taught for example in U.S. Pat. Nos. 5,597,936, and 5,595,967.

Compositions herein may also suitably include a transition metal complex of ligands such as bispidones (WO 05/042532 A1) and/or macropolycyclic rigid ligands—abbreviated as "MRLs". As a practical matter, and not by way of limitation, the compositions and processes herein can be adjusted to provide on the order of at least one part per hundred million of the active MRL species in the aqueous washing medium, and will typically provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include, for example, manganese, iron and chromium. Suitable MRLs include 5,12-diethyl-1,5,8,12-tetraazabicyclo[6.6.2]hexadecane.

Suitable transition metal MRLs are readily prepared by known procedures, such as taught for example in WO 00/32601, and U.S. Pat. No. 6,225,464.

Solvents—Suitable solvents include water and other solvents such as lipophilic fluids. Examples of suitable lipophilic fluids include siloxanes, other silicones, hydrocarbons, glycol ethers, glycerine derivatives such as glycerine ethers, perfluorinated amines, perfluorinated and hydrofluoroether solvents, low-volatility nonfluorinated organic solvents, diol solvents, other environmentally-friendly solvents and mixtures thereof. In some embodiments, the solvent includes water. The water can include water from any source including deionized water, tap water, softened water, and combinations thereof. Solvents are typically present at from about 0.1% to about 50%, or from about 0.5% to about 35%, or from about 1% to about 15% by weight.

Form of the Compositions

The detergent compositions of the present invention may be of any suitable form, including paste, liquid, solid (such as tablets, powder/granules), foam or gel, with powders and tablets being preferred. The composition may be in the form of a unit dose product, i.e. a form which is designed to be used as a single portion of detergent composition in a washing operation. Of course, one or more of such single portions may be used in a cleaning operation.

Solid forms include, for example, in the form of a tablet, rod, ball or lozenge. The composition may be a particulate form, loose or pressed to shape or may be formed by injection moulding or by casting or by extrusion. The composition may be encased in a water soluble wrapping, for, example of PVOH or a cellulosic material. The solid product may be provided as a portioned product as desired.

The composition may also be in paste, gel or liquid form, including unit dose (portioned products) products. Examples include a paste, gel or liquid product at least partially surrounded by, and preferably substantially enclosed in a water-soluble coating, such as a polyvinyl alcohol package. This package may for instance take the form of a capsule, a pouch or a moulded casing (such as an injection moulded casing) etc. Preferably the composition is substantially surrounded by such a package, most preferably totally surrounded by such a package. Any such package may contain one or more product formats as referred to herein and the package may contain one or more compartments as desired, for example two, three or four compartments.

If the composition is a foam, a liquid or a gel it is preferably an aqueous composition although any suitable solvent may be used. According to an especially preferred embodiment of the present invention the composition is in the form of a tablet, most especially a tablet made from compressed particulate material.

If the compositions are in the form of a viscous liquid or gel they preferably have a viscosity of at least 50 mPas when measured with a Brookfield RV Viscometer at 25° C. with Spindle 1 at 30 rpm.

The compositions of the invention will typically be used by placing them in a detergent dispenser e.g. in a dishwasher machine draw or free standing dispensing device in an automatic dishwashing machine. However, if the composition is in the form of a foam, liquid or gel then it may be applied to by any additional suitable means into the dishwashing machine, for example by a trigger spray, squeeze bottle or an aerosol.

Processes of Making Cleaning Compositions

The compositions of the invention may be made by any suitable method depending upon their format. Suitable manufacturing methods for detergent compositions are well known in the art, non-limiting examples of which are described in U.S. Pat. Nos. 5,879,584; 5,691,297; 5,574,005; 5,569,645; 5,565,422; 5,516,448; 5,489,392; and 5,486,303. Various techniques for forming detergent compositions in solid forms are also well known in the art, for example, detergent tablets may be made by compacting granular/particular material and may be used herein.

In one aspect, the liquid detergent compositions disclosed herein may be prepared by combining the components thereof in any convenient order and by mixing, e.g., agitating, the resulting component combination to form a phase stable liquid detergent composition. In one aspect, a liquid matrix is formed containing at least a major proportion, or even substantially all, of the liquid components, with the liquid components being thoroughly admixed by imparting shear agitation to this liquid combination. For example, rapid stirring with a mechanical stirrer may usefully be employed. While shear agitation is maintained, substantially all of any anionic surfactant and the solid ingredients can be added. Agitation of the mixture is continued, and if necessary, can be increased at this point to form a solution or a uniform dispersion of insoluble solid phase particulates within the liquid phase. After some or all of the solid-form materials have been added to this agitated mixture, particles of any enzyme material to be included, e.g., enzyme prills are incorporated. As a variation of the composition preparation procedure described above, one or more of the solid components may be added to the agitated mixture as a solution or slurry of particles premixed with a minor portion of one or more of the liquid components. After addition of all of the composition components, agitation of the mixture is continued for a period of time sufficient to form compositions having the requisite viscosity and phase stability characteristics. Frequently this will involve agitation for a period of from about 30 to 60 minutes.

Reduction of Smoking in Laundry Fabrics

There have been reports of undesirable smoking issues for laundry particularly when a washed fabric comes in contact with a hot iron. This is due to a switch from nonyl phenol ethoxylate (NPE) based detergents to alcohol phenol ethoxylate (APE) based detergents. The problem is due to the residual unreacted long chain alcohols which are highly soluble in APE based detergents. It is well known in the surfactant industry that APEs are more monodisperse and have less unreacted alcohol than the AEs, because the starting alkyl phenols are more reactive than the starting linear alcohols. The use solution cannot suspend all the highly insoluble unreacted alcohol, which deposits onto a washed fabric and can cause smoking when the fabric comes in contact with a hot iron.

The extended surfactants and microemulsions of the present invention undergo two steps of alkoxylation (first propoxylation or butoxylation, then followed with ethoxylation) and therefore have reduced levels of residual (unreacted) alcohol, specifically below 0.1%. Thus after the laundry process, the extended surfactants and microemulsions of the present invention leave less residue from the highly insoluble long chain alcohols onto the washed fabric, which in turn greatly reduces the smoking when these washed fabrics come in contact with hot irons.

The present invention is more particularly described in the following examples that are intended as illustrations only, since numerous modifications and variations within the scope of the present invention will be apparent to those skilled in the art. Unless otherwise noted, all parts, percentages, and ratios reported in the following examples are on a weight basis, and all reagents used in the examples were obtained, or are available, from the chemical suppliers described below, or may be synthesized by conventional techniques. All references cited herein are hereby incorporated in their entirety by reference.

EXAMPLE 1

(I) Commercial Extended Surfactants:

| Extended Surfactants | Vendor | % Active | Structure |
|---|---|---|---|
| Plurafac SL-42 | BASF | 100 | $C_{6-10}$—$(PO)_3(EO)_6$ |
| Plurafac SL-62 | BASF | 100 | $C_{6-10}$—$(PO)_3(EO)_8$ |
| Lutensol XL-40 | BASF | 100 | $C_{10}$—$(PO)_a(EO)_b$ series |
| Lutensol XL-50 | BASF | 100 | |
| Lutensol XL-60 | BASF | 100 | |
| Lutensol XL-70 | BASF | 100 | |
| Lutensol XL-79 | BASF | 85 | |
| Lutensol XL-80 | BASF | 100 | |
| Lutensol XL-89 | BASF | 80 | |
| Lutensol XL-90 | BASF | 100 | |
| Lutensol XL-99 | BASF | 80 | |
| Lutensol XL-100 | BASF | 100 | |
| Lutensol XL-140 | BASF | 100 | |
| Ecosurf EH-3 | Dow | 100 | 2-Ethyl Hexyl $(PO)_m(EO)_n$ series |
| Ecosurf EH-6 | Dow | 100 | |
| Ecosurf EH-9 | Dow | 100 | |
| Ecosurf SA-4 | Dow | 100 | $C_{6-12}(PO)_{3-4}(EO)_4$ |
| Ecosurf SA-7 | Dow | 100 | $C_{6-12}(PO)_{3-4}(EO)_7$ |
| Ecosurf SA-9 | Dow | 100 | $C_{6-12}(PO)_{3-4}(EO)_9$ |
| Surfonic PEA-25 | Huntsman | 100 | $C_{12-14}(PO)_2N[(EO)_{2.5}]_2$ |
| X-AES | Huntsman | 23 | $C_{12-14}$—$(PO)_{16}$-$(EO)_2$-sulfate |
| X-LAE | Huntsman | 100 | $C_{12-14}$—$(PO)_{16}(EO)_{12}$ |
| Alfoterra 123-4S | Sasol | 30 | $C_{12-13}$—$(PO)_4$-sulfate |
| Alfoterra 123-8S | Sasol | 30 | $C_{12-13}$—$(PO)_8$-sulfate |
| Marlowet 4561 | Sasol | 90 | C16-C18-alcohol polyalkylene glycol ether carboxylic acids |
| Marlowet 4560 | Sasol | 90 | C16-C18-alcohol polyalkylene glycol ether carboxylic acids |
| Marlowet 4539 | Sasol | 90 | C9-alcohol polyethylene glycol ether liquid carboxylic acids |

According to the invention it was discovered that two non-ionic extended surfactants Plurafac SL-42 and SL-62, formed clear homogeneous microemulsions with extended heating.

Furthermore, unlike ordinary phase inversion induced microemulsions which revert after the temperature cool down, the new microemulsions are not reversible.

Equal % Water/Oil/Surfactant Microemulsions:
Microemulsions were formed with hexadecane, water and surfactant. The results are shown in table 2.

TABLE 2

Hydrocarbon based microemulsions:
MICROEMULSION STUDY
Hexadecane Study

| Oct. 30, 2008 | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|
| % Raw Material | | | | | | | | | | | | | | | | |
| DI water | 43.5 | 40.0 | 36.4 | 33.3 | 40.0 | 36.4 | 33.3 | 43.5 | 43.5 | 40.0 | 36.4 | 33.3 | 43.5 | 40.0 | 36.4 | 33.3 |
| EcoSurf SA-4 | | | | | | | | | 13.0 | 20.0 | 27.3 | 33.3 | | | | |
| EcoSurf SA-7 | | | | | | | | | | | | | 13.0 | 20.0 | 27.3 | 33.3 |
| EcoSurf SA-9 | | | | | | | | | | | | | | | | |
| Hexadecane | 43.5 | 40.0 | 36.4 | 33.3 | 40.0 | 36.4 | 33.3 | 43.5 | 43.5 | 40.0 | 36.4 | 33.3 | 43.5 | 40.0 | 36.4 | 33.3 |
| NaCl | | | | | | | | | | | | | | | | |
| Salt water (.38%) | | | | | | | | | | | | | | | | |
| PEA-25 | 13.0 | 20.0 | 27.3 | 33.3 | | | | | | | | | | | | |
| Salt water, (0.1%) | | | | | | | | | | | | | | | | |
| SL-42 | | | | | | | | | | | | | | | | |
| SL-62 | | | | | | | | | | | | | | | | |
| Surfonic 24-5 | | | | | 20.0 | 27.3 | 33.3 | 13.0 | | | | | | | | |
| X-AES (lot #39) | | | | | | | | | | | | | | | | |
| X-AES (lot #62) | | | | | | | | | | | | | | | | |
| TOTAL | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 |
| % NaCl | | | | | | | | | | | | | | | | |
| Microemulsion | | YES | YES | YES | YES | YES | YES | | | | YES | YES | | | | YES |
| Max temp, F. ° | | | 126 | 130 | 140 | 140 | 152 | | | | 114 | 120 | | | | 180 |
| Min Temp, F. ° | | | 102 | <80 | 116 | 110 | | | | | 84 | 80 | | | | 145 |
| Appearance | | | | Gel @ 74° | Gel | Gel | Gel | | | | | | | | | Gel |
| uEM at 23 days | | | | No | No | No | No | | | | No | Yes | | | | No |
| uEM at 26 days | | | | | | | | | | | | | | | | |

| Oct. 30, 2008 | 32 | 33 | 34 | 35 | 36 | 27 | 28 | 39 | 40 | 41 | 42 | 43 | 44 | 45 |
|---|---|---|---|---|---|---|---|---|---|---|---|---|---|---|
| % Raw Material | | | | | | | | | | | | | | |
| DI water | 43.5 | 40.0 | 36.4 | 33.3 | 43.5 | 40.0 | 36.4 | 33.3 | 43.5 | 40.0 | 36.4 | 33.3 | 0.0 | 22.6 |
| EcoSurf SA-4 | | | | | | | | | | | | | | |
| EcoSurf SA-7 | | | | | | | | | | | | | | |
| EcoSurf SA-9 | 13.0 | 20.0 | 27.3 | 33.3 | | | | | | | | | | |
| Hexadecane | 43.5 | 40.0 | 36.4 | 33.3 | 43.5 | 40.0 | 36.4 | 33.3 | 43.5 | 40.0 | 36.4 | 33.3 | 45.3 | 45.3 |
| NaCl | | | | | | | | | | | | | 0.4 | 0.4 |
| Salt water (.38%) | | | | | | | | | | | | | | |
| PEA-25 | | | | | | | | | | | | | | |
| Salt water, (0.1%) | | | | | | | | | | | | | 45.3 | 22.6 |
| SL-42 | | | | | | | | | | | | | | |
| SL-62 | | | | | | | | | | | | | | |
| Surfonic 24-5 | | | | | | | | | | | | | | |
| X-AES (lot #39) | | | | | 13.0 | 20.0 | 27.3 | 33.3 | | | | | | |
| X-AES (lot #62) | | | | | | | | | 13.0 | 20.0 | 27.3 | 33.3 | 9.1 | 9.1 |
| TOTAL | 100.0 | 100.0 | 100.0 | 100.0 | 100.0 | 100.0 | 100.0 | 100.0 | 100.0 | 100.0 | 100.0 | 100.0 | 100.0 | 100.0 |
| % NaCl | | | | | | | | | | | | | | |
| Microemulsion | | | | | | | | | | | | | | |
| Max temp, F. ° | | | | | | | | | | | | | | |
| Min Temp, F. ° | | | | | | | | | | | | | | |
| Appearance | | | | | | | | | | | | | | |
| uEM at 23 days | | | | | | | | | | | | | | |
| uEM at 26 days | | | | | | | | | | | | | | |

| Oct. 30, 2008 | 46 | 47 | 48 | 49 | 50 | 51 | 52 | 53 | 54 | 55 | 56 | 57 | 58 |
|---|---|---|---|---|---|---|---|---|---|---|---|---|---|
| % Raw Material | | | | | | | | | | | | | |
| DI water | 44.2 | 11.3 | 34.0 | 36.2 | 9.1 | 45.3 | 30.2 | 15.1 | 43.5 | 40.0 | 36.4 | 33.3 | 43.5 |
| EcoSurf SA-4 | | | | | | | | | | | | | |
| EcoSurf SA-7 | | | | | | | | | | | | | |
| EcoSurf SA-9 | | | | | | | | | | | | | |
| Hexadecane | 45.3 | 45.3 | 45.3 | 45.3 | 45.3 | 45.3 | 45.3 | 45.3 | 43.5 | 40.0 | 36.4 | 33.3 | 43.5 |
| NaCl | 0.4 | 0.4 | 0.4 | 0.4 | 0.4 | 0.4 | 0.4 | 0.4 | | | | | |
| Salt water (.38%) | | | | | | | | | | | | | |
| PEA-25 | | | | | | | | | | | | | |
| Salt water, (0.1%) | 1.1 | 34.0 | 11.3 | 9.1 | 36.2 | 0.0 | 15.1 | 30.2 | | | | | |
| SL-42 | | | | | | | | | | | | | 13.0 |
| SL-62 | | | | | | | | | 13.0 | 20.0 | 27.3 | 33.3 | |

TABLE 2-continued

Hydrocarbon based microemulsions:
MICROEMULSION STUDY
Hexadecane Study

| | | | | | | | | | | | | | |
|---|---|---|---|---|---|---|---|---|---|---|---|---|---|
| Surfonic 24-5 | | | | | | | | | | | | | |
| X-AES (lot #39) | | | | | | | | | | | | | |
| X-AES (lot #62) | 9.1 | 9.1 | 9.1 | 9.1 | 9.1 | 9.1 | 9.1 | 9.1 | | | | | |
| TOTAL | 100.0 | 100.0 | 100.0 | 100.0 | 100.0 | 100.0 | 100.0 | 100.0 | 100.0 | 100.0 | 100.0 | 100.0 | |
| % NaCl | | | | | | | | | | | | | |
| Microemulsion | | | | | | | | | | | | | |
| Max temp, F. ° | | | | | | | | | | | | | |
| Min Temp, F. ° | | | | | | | | | | | | | |
| Appearance | | | | | | | | | | | | | |
| uEM at 23 days | | | | | | | | | | | | | |
| uEM at 26 days | | | | | | | | | | | | | |

| | Oct. 30, 2008 | 59 | 60 | 61 | 62 | 63 | 64 | 65 | 66 | 67 | 68 | 69 |
|---|---|---|---|---|---|---|---|---|---|---|---|---|
| % Raw Material | | | | | | | | | | | | |
| DI water | | 40.0 | 36.4 | 33.3 | | | | | | | | |
| EcoSurf SA-4 | | | | | | | | | | | | |
| EcoSurf SA-7 | | | | | | | | | | | | |
| EcoSurf SA-9 | | | | | | | | | | | | |
| Hexadecane | | 40.0 | 36.4 | 33.3 | 43.5 | 40.0 | 36.4 | 33.3 | 43.5 | 40.0 | 36.4 | 33.3 |
| NaCl | | | | | | | | | | | | |
| Salt water (.38%) | | | | | | | | | | | | |
| PEA-25 | | | | | | | | | | | | |
| Salt water, (0.1%) | | | | | | 43.5 | 40.0 | 36.4 | 33.3 | 43.5 | 40.0 | 36.4 | 33.3 |
| SL-42 | | 20.0 | 27.3 | 33.3 | | | | | 13.0 | 20.0 | 27.3 | 33.3 |
| SL-62 | | | | | 13.0 | 20.0 | 27.3 | 33.3 | 0.0 | 0.0 | | |
| Surfonic 24-5 | | | | | | | | | | | | |
| X-AES (lot #39) | | | | | | | | | | | | |
| X-AES (lot #62) | | | | | | | | | | | | |
| TOTAL | | 100.0 | 100.0 | 100.0 | 100.0 | 100.0 | 100.0 | 100.0 | 100.0 | 100.0 | 100.0 | 100.0 |
| % NaCl | | | | 0.000 | | | | | | | | 0.033 |
| Microemulsion | | | | YES | | | | | | | | YES |
| Max temp, F. ° | | | | 170 | | | | | | | | 170 |
| Min Temp, F. ° | | | | 145 | | | | | | | | 145 |
| Appearance | | | | | | | | | | | | |
| uEM at 23 days | | | | | | | | | | | | |
| uEM at 26 days | | | | No | | | | | | | | |

These data show that in general both regular and extended surfactants can form microemulsions with hydrocarbon type oils such as hexadecane, especially those with a phase inversion temperature (which is usually within a few degree of the cloud point) matching the study temperature.

Triglyceride Based Microemulsions

It is generally known that it is difficult to form triglyceride based microemulsions. Table 3 shows that while we can form hydrocarbon based microemulsions with a series of surfactants including extended surfactants, the same surfactants all fail to form triglyceride based microemulsions.

TABLE 3

| | 18 % | 19 % | 20 % | 21 % | 22 % | 26 % | 27 % | 31 % | 61 % | 69 % |
|---|---|---|---|---|---|---|---|---|---|---|
| DI water | 36.4 | 33.3 | 40.0 | 36.4 | 33.3 | 36.4 | 33.3 | 33.3 | 33.3 | |
| Salt water, (0.1%) | | | | | | | | | | 33.3 |
| Hexadecane | 36.4 | 33.3 | 40.0 | 36.4 | 33.3 | 36.4 | 33.3 | 33.3 | 33.3 | 33.3 |
| EcoSurf SA-4 | | | | | | 27.3 | 33.3 | | | |
| EcoSurf SA-7 | | | | | | | | 33.3 | | |
| PEA-25 | 27.3 | 33.3 | | | | | | | | |
| SL-42 | | | | | | | | | 33.3 | 33.3 |
| Surfonic 24-5 | | | 20.0 | 27.3 | 33.3 | | | | | |
| TOTAL | 100.0 | 100.0 | 100.0 | 100.0 | 100.0 | 100.0 | 100.0 | 100.0 | 100.0 | 100.0 |
| % NaCl | 0.000 | 0.000 | 0.000 | 0.000 | 0.000 | 0.000 | 0.000 | 0.000 | 0.000 | 0.033 |
| Microemulsion | YES | YES | YES | YES | YES | YES | YES | YES | YES | YES |
| Max temp, F. ° | 126 | 130 | 140 | 140 | 152 | 114 | 120 | 180 | 170 | 170 |
| Min Temp, F. ° | 102 | <80 | 116 | 110 | 76 | 84 | 80 | 145 | 145 | 145 |
| | | gel @ 74° | gel | gel | gel | | | gel | gel | gel |

| 71 % | 72 % | 73 % | 74 % | 75 % | 76 % | 77 % | 78 % | 70 % |
|---|---|---|---|---|---|---|---|---|

TABLE 3-continued

| | | | | | | | | | |
|---|---|---|---|---|---|---|---|---|---|
| Salt water (.13%) | 36.4 | 33.3 | 40.0 | 36.4 | 33.3 | 36.4 | 33.3 | 33.3 | 33.3 |
| Soybean Oil | 36.4 | 33.3 | 40.0 | 36.4 | 33.3 | 36.4 | 33.3 | 33.3 | 33.3 |
| EcoSurf SA-4 | | | | | | 27.3 | 33.3 | | |
| EcoSurf SA-7 | | | | | | | | 33.3 | |
| PEA-25 | 27.3 | 33.3 | | | | | | | |
| SL-42 | | | | | | | | | 33.3 |
| Surfonic 24-5 | | | 20.0 | 27.3 | 33.3 | | | | |
| TOTAL | 100.0 | 100.0 | 100.0 | 100.0 | 100.0 | 100.0 | 100.0 | 100.0 | 100.0 |
| % NaCl | 0.047 | 0.043 | 0.052 | 0.047 | 0.043 | 0.047 | 0.043 | 0.043 | 0.043 |
| Microemulsion | NO | NO | NO | NO | NO | NO | NO | NO | NO |

Table 4 below shows additional surfactants (some are extended surfactants) that also failed to form triglyceride based microemulsions.

TABLE 4

Barlox 12
Naxon DIL, 40%
X-AES (lot #39)
X-LAE
XL-89
XP-99

Applicants discovered that two nonionic extended surfactants Plurafac SL-42 and SL-62, could form clear homogeneous microemulsions with extended heating. Furthermore, unlike ordinary phase inversion induced microemulsions which revert after the temperature cool down, the new microemulsions are not reversible.

Table 5 shows the compositions. The processes of forming the microemulsions are characterized by time (of heating), temperature, and conductivity (Tables 6-9 and corresponding FIGS. 1-7. Interestingly, all exhibit a general trend—with prolonged heating, conductivity first increases, reaches a peak, then drops and stay at a very low level. This suggests initially oil-in-water nature, and eventually water-in-oil nature with prolonged heating. In these studies, the small level of salt was used as a conductivity marker only (does not affect the microemulsion formation).

TABLE 5

| Microemulsion Formed | FORMULA #70 | FORMULA #57 |
|---|---|---|
| salt Water, .13% | 33.3 | 33 |
| SL-42 | 33.3 | |
| SL-62 | | 33 |
| Soybean Oil | 33.3 | 33 |
| TOTAL | 99.9 | 99 |

TABLE 6

DATA SET #1 Oct. 8, 2008
lot # SL-42 031008

| 1% Cloud Pt., F. TEMP | ? #70 COND, uS |
|---|---|
| 78 | 133.6 |
| 88 | 147.5 |
| 90 | 168.4 |
| 96 | 170.7 |
| 100 | 173.8 |
| 104 | 178.9 |

TABLE 6-continued

DATA SET #1 Oct. 8, 2008
lot # SL-42 031008

| 1% Cloud Pt., F. TEMP | ? #70 COND, uS |
|---|---|
| 108 | 185.5 |
| 112 | 192.3 |
| 116 | 199.6 |
| 118 | 209.3 |
| 120 | 214.1 |
| 124 | 222.8 |
| 128 | 226.8 |
| 132 | 226.8 |
| 140 | 226 |
| 144 | 226.7 |
| 146 | 277.9 |
| 150 | 339.2 |
| 154 | 335.5 |
| 156 | 325.2 |
| 158 | 294.7 |
| 160 | 266.1 |
| 166 | 228.6 |
| 170 | 171.8 |
| 171 | 128.5 |
| 172 | 110.3 |
| 173 | 78.96 |
| 174 | 45.52 |
| 176 | 17 |
| 178 | 9 |
| 180 | 7.881 |
| 182 | 3.627 |
| 183 | 1.371 |
| 184 | 0.9697 |
| **72 | 0.4697 |

**Conductivity after 24 hours, solution still microemulsion

TABLE 7

DATA SET #2 Oct. 21, 2008
SL-42 lot # 042507

| 1% Cloud Pt., F. TEMP | 142 #70 COND, uS | minutes | comments |
|---|---|---|---|
| 79 | 110.8 | 0 | |
| 80 | 118.1 | 1 | |
| 86 | 122.7 | 2 | |
| 90 | 125.7 | 4 | |
| 110 | 180.5 | 10 | |
| 124 | 205.6 | 17 | |
| 130 | 232.4 | 23 | |
| 134 | 256.2 | 24 | |
| 138 | 271.8 | 25 | |
| 150 | 290.2 | 30 | |
| 152 | 374.2 | 45 | |
| 149 | 284.2 | 55 | |
| 149 | 269.1 | 65 | |
| 149 | 50.33 | 135 | |

TABLE 7-continued

DATA SET #2 Oct. 21, 2008
SL-42 lot # 042507

| TEMP | 142 #70 COND, uS | minutes | comments |
|---|---|---|---|
| 1% Cloud Pt., F. | | | |
| 151 | 7.988 | 150 | u EM formed |
| 150 | 3.96 | 155 | |
| 150 | 1.322 | 165 | |
| 150 | 1.094 | 167 | hazy/cloudy |
| 108 | 1.396 | 180 | clear u EM again |
| 106 | 0.9196 | 183 | |
| 82 | 0.5963 | 205 | |
| **72 | 0.2954 | | |

**Conductivity after 24 hours, solution still microemulsion

TABLE 8

DATA SET #3 Oct. 22, 2008
SL-42 lot nuber 052804

| TEMP | 148 #70 COND, uS | minutes |
|---|---|---|
| 82 | 157.60 | 0 |
| 90 | 148.00 | |
| 100 | 181.20 | |
| 110 | 198.20 | |
| 120 | 238.60 | |
| 130 | 267.60 | 24 |
| 140 | 302.60 | |
| 150 | 330.30 | 33 |
| 152 | 374.60 | 36 |
| 148 | 333.30 | 56 |
| 148 | 325.20 | 80 |
| 150 | 254.10 | 129 |
| 149 | 231.30 | 130 |
| 149 | 208.90 | 141 |
| 149 | 187.90 | 150 |
| 150 | 120.50 | 178 |
| 150 | 110.40 | 182 |
| 150 | 86.98 | 190 |
| 150 | 54.81 | 205 |
| 150 | 21.82 | 220 |
| 150 | 10.51 | 229 |
| 152 | 7.305 | 231 |
| 152 | 5.434 | 234 |
| 152 | 3.702 | 236 |
| 152 | 2.487 | 243 |
| 140 | 2.376 | 245 |
| 116 | 9.713 | 262 |
| **72 | 0.9872 | |

**Conductivity after 24 hours, solution still microemulsion

TABLE 9

TRIAL 2
Oct. 29, 2008
lot # SL-62 30125737

| TEMP | COND, uS | time, min |
|---|---|---|
| 102 | 139.1 | 0 |
| 112 | 161 | 3 |
| 120 | 192.2 | 5 |
| 144 | 262.7 | 11 |
| HOLD AT RT OVERNIGHT, RESTART NEXT AM | | |
| 80 | 59.58 | 0 |
| 88 | 62.61 | 2 |
| 106 | 83.87 | 11 |
| 140 | 130.3 | 18 |
| 150 | 155.8 | 21 |
| 160 | 212.7 | 25 |
| 155 | 169.4 | 29 |
| 142 | 126 | 36 |
| 150 | 115.1 | 41 |
| 156 | 109.5 | 43 |
| 158 | 95.79 | 45 |
| 154 | 79.05 | 48 |
| 153 | 54.81 | 52 |
| 154 | 44.09 | 55 |
| 155 | 18.02 | 65 |
| 168 | 14.89 | 72 |
| 158 | 6.606 | 81 |
| 134 | 1.664 | 93 |
| 140 | 0.9824 | 106 |

(III) Effect of pH Vs. Time of uEM:

In an effort to optimize the microemulsion forming formulas, we have made a series of compositions containing extended surfactants (X-AES and Plurafac SL-42) and linker surfactant (C12 AO), soybean oil, and various levels of chelating agent. The goal was to find the optimal chelating agent to form soybean oil based microemulsions. From these experiments we have surprisingly discovered that pH decreases significantly with time, and some compositions become one phase with time (in other words, becoming true microemulsions). These data are summarized in Table 10 below. Furthermore, compositions stored at an elevated temperature exhibit similar changes, except at a faster rate.

These results suggest that the soybean oil is undergoing hydrolysis, forming fatty acids, di- and mono-triglycerides.

TABLE 10

Non-transfat treatment and removal studies pH vs time

| Formula # and start date: | % Trilon M 2501 48 | % EDTA 2501 07 | % SOYBEAN OIL Sodexo | Days | | | | | |
|---|---|---|---|---|---|---|---|---|---|
| | | | | 0 | 1 | 4 | 5 pH | 6 | 10 | 56 |
| AMBIENT | | | | | | | | | | |
| 1 (Feb. 13, 2009) | 10 | | 9.6 | | | | | | | 10.74 |
| 2 (Feb. 13, 2009) | 15 | | 9.6 | | | | | | | 10.8 |

TABLE 10-continued

Non-transfat treatment and removal studies pH vs time

| | % | % | % | Days | | | | | | |
|---|---|---|---|---|---|---|---|---|---|---|
| Formula # and start date: | Trilon M 2501 48 | EDTA 2501 07 | SOYBEAN OIL Sodexo | 0 | 1 | 4 | 5 pH | 6 | 10 | 56 |
| 3 (Feb. 13, 2009) | 20 | | 9.6 | | | | | | | 10.73 |
| 4 (Feb. 13, 2009) | 25 | | 9.6 | | | | | | | 10.76 |
| 5 (Feb. 13, 2009) | 30 | | 9.6 | | | | | | | 10.69 |
| 6 (Feb. 13, 2009) | | 10 | 9.6 | | | | | | | 10.39 |
| 7 (Feb. 13, 2009) | | 15 | 9.6 | | | | | | | 10.46 |
| 8 (Feb. 13, 2009) | | 20 | 9.6 | | | | | | | 10.39 |
| 9 (Feb. 13, 2009) | | 25 | 9.6 | | | | | | | 10.39 |
| 10 (Feb. 13, 2009) | | 30 | 9.6 | | | | | | | 10.37 |
| 1 (Apr. 10, 2009) | 10 | | 9.6 | 12.02 | | 11.33 | 11.28 | 11.1 | | |
| 5 (Apr. 10, 2009) | 30 | | 9.6 | 12.85 | | 11.3 | 11.23 | 11.04 | | |
| 6 (Apr. 10, 2009) | | 10 | 9.6 | 12.62 | | 12.05 | 11.92 | 11.37 | | |
| 10 (Apr. 10, 2009) | | 30 | 9.6 | 13.23 | | 11.86 | 11.22 | 11.15 | | |
| 1 (Apr. 14, 2009) | 10 | | 9.6 | 11.99 | 11.61 | | | 11.21 | | |
| 5 (Apr. 14, 2009) | 30 | | 9.6 | 12.81 | 11.81 | | | 11.18 | | |
| 6 (Apr. 14, 2009) | | 10 | 9.6 | 12.54 | 12.36 | | | 11.81 | | |
| 10 (Apr. 14, 2009) | | 30 | 9.6 | 13.23 | 12.45 | | | 11.49 | | |
| 150 F. | | | | | | | | | | |
| 1 (Feb. 13, 2009) | | | | | | | | | | 9.77 |
| 2 (Feb. 13, 2009) | | | | | | | | | | 9.84 |
| 3 (Feb. 13, 2009) | | | | | | | | | | 9.76 |
| 4 (Feb. 13, 2009) | | | | | | | | | | 9.74 |
| 5 (Feb. 13, 2009) | | | | | | | | | | 10.01 |
| 6 (Feb. 13, 2009) | | | | | | | | | | 9.47 |
| 7 (Feb. 13, 2009) | | | | | | | | | | 9.56 |
| 8 (Feb. 13, 2009) | | | | | | | | | | 9.56 |
| 9 (Feb. 13, 2009) | | | | | | | | | | 9.54 |
| 10 (Feb. 13, 2009) | | | | | | | | | | 9.55 |
| 1 (Apr. 14, 2009) | 10 | | 9.6 | 11.99 | | | | | 10.38, clear | |
| 5 (Apr. 14, 2009) | 30 | | 9.6 | 12.81 | | | | | 10.31, sep | |
| 6 (Apr. 14, 2009) | | 10 | 9.6 | 12.54 | | | | | 10.33, clear | |
| 10 (Apr. 14, 2009) | | 30 | 9.6 | 13.23 | | | | | 10.18, sep | |

(IV) Fatty Acid Enhanced uEM Formation:
Test Plan for the Role of Free Fatty Acid in the Formation of Microemulsions with Non-trans Fats for Enhanced Soil Removal:

We have previously confirmed a slow, heat required (around 140-180 F), virtually irreversible microemulsion formation with

| Microemulsion Formed | FORMULA #70 | FORMULA #57 |
|---|---|---|
| salt Water, .13% | 33.3 | 33 |
| SL-42 | 33.3 | |
| SL-62 | | 33 |
| Soybean Oil | 33.3 | 33 |
| TOTAL | 99.9 | 99 |

Based on some recent test results that showed potential evidence of hydrolysis of non-trans fat during wash at 150 F, we speculate that the above described microemulsions may have been aided by the free fatty acids generated from the hydrolysis of the soybean oil. Therefore, if we add the appropriate free fatty acid to the composition, we may have rapid formation of microemulsions and thus enhanced removal of these non-trans fats.

Test Plan:
(1) Re-make Formula #70 at room temperature with stirring, add subsequent quantified small doses of isononanoic acid, and observe if microemulsion can be formed. Also observe if the branched isononanoic acid helps reduce the overall viscosity.
(2) Repeat (1) at 120 F.
(3) Repeat (1) with lauric acid at a temperature slightly above the melting point of lauric acid.
(4) Repeat (1) with other saturated free fatty acids (including branched ones).

The results are summarized in table 11 below. These results confirm that we can form virtually instantaneous room temperature soybean oil based microemulsions with extended surfactants and fatty acids. Those with very high viscosity and gelling and high conductivity are not considered true microemulsions. The preferred fatty acids are isononanoic acid and dicarboxylic fatty acid because the resultant microemulsions have low viscosities.

TABLE 11

Free fatty acid enhanced microemulsion formations
Rest of composition is equal parts Plurafac SL-42,
soybean oil, and 0.13% salt water

| Fatty Acid used | % at which phase inversion occurs (conductivity undergoes big change, and the mixture becomes relatively clear) | Conductivity, uS | Observation |
|---|---|---|---|
| Isononanoic acid | 18 | 4.9 | clear, thin |
| Lauric acid | 15 | 1.1 | semi-white to clear |
| Coconut Fatty acid | 21 | 8 | thick, opaque, viscous, white |

TABLE 11-continued

Free fatty acid enhanced microemulsion formations
Rest of composition is equal parts Plurafac SL-42,
soybean oil, and 0.13% salt water

| Fatty Acid used | % at which phase inversion occurs (conductivity undergoes big change, and the mixture becomes relatively clear) | Conductivity, uS | Observation |
|---|---|---|---|
| Dicarboxylic Fatty acid | 19 | 37 | thin, white |
| Octanoic Acid | 20 | 6.3 | clear, thin |
| Decanoic Acid | 40 | 0.23 | semi-clear/white |
| Oleic Acid | 10 | 129 | gelled |
| Oleic Acid w/MEA | 7 | 422 | gelled |
| Oleic Acid w/NaOH | 7 | 437 | gelled |
| Oleic Acid w/KOH | 13 | 671 | gelled |
| SLA | 17 | 1040 | opaque, viscous |

(V) Other Non-ionic Extended Surfactant Data with Tegin ISO as Linker Surfactant:

The free fatty acids are not very efficient in assisting the formation of microemulsions, requiring a high level (about ½ of the level of extended surfactants). We also speculated that the level of hydrolysis during the extended heating experiments with no alkalinity (described in Section (II) above) is not very extensive, therefore, the di- and mono-triglycerides formed from the hydrolysis, rather than the free fatty acids, may be more responsible.

One prime candidate has been sourced as Tegin ISO.
TEGIN® ISO—Isostearic mono/diglyceride Some formation of new soybean oil based microemulsions with various non-ionic extended surfactants and Tegin as linker co-surfactants are summarized in Table 12-16 below. The results clearly show that Tegin ISO is more efficient than the free fatty acids. The ratio of non-ionic extended surfactant to Tegin ISO is about 7:1 instead of 2:1 for the free fatty acids:

TABLE 12

Formula-70-EH9-28-5

| | | |
|---|---|---|
| NaCL 0.13% | | 33.3 |
| Soy Oil | | 33.3 |
| Ecosurf EH-9 | | 28.3 |
| Tegin ISO | 5 ml = 4.25 g | 4.25 |
| Total | | 99.15 |

Date: Jul. 10, 2009
Upon Mixing:
Went into stiff solid/gel white

| Cloud Point: TEMP F. | Temp C. | Cond, uS | Elapsed Time, min | State/Conditions |
|---|---|---|---|---|
| 77.0 | 25.0 | 288.10 | 5 | thin white opaque |
| 83.4 | 28.5 | 294.30 | 7 | phase chg on bottom |
| 165.2 | 74.0 | 273.10 | 10 | same |
| 154.0 | 68.0 | 234.90 | 20 | back to milky white |
| 165.2 | 74.0 | 193.50 | 25 | almost phase chg on bottom again |
| 172.4 | 78.0 | 204.10 | 25 | same |
| 174.2 | 79.0 | 196.50 | 25 | same |
| 176.0 | 80.0 | 173.50 | 26 | same |
| 174.2 | 79.0 | 130.30 | 28 | bottom is clear |
| 170.6 | 77.0 | 60.200 | 29 | same |
| 174.2 | 79.0 | 31.890 | 34 | same |
| 172.4 | 78.0 | 40.790 | 37 | clear like uEM ? |
| 174.2 | 79.0 | 40.380 | 39 | clear like uEM ? |
| 170.6 | 77.0 | 29.070 | 40 | foggy again |
| 168.8 | 76.0 | 19.550 | 41 | same |
| 165.2 | 74.0 | 14.680 | 43 | same |
| 185.9 | 85.5 | 3.6230 | 45 | same |
| 190.4 | 88.0 | 1.5030 | 47 | same |
| 197.6 | 92.0 | 1.0010 | 50 | hydrolysis product yellow clear uEM yes |
| 199.4 | 93.0 | 1.0340 | 52 | hydrolysis product yellow clear uEM yes |
| 204.0 | 95.6 | 0.9664 | 55 | hydrolysis product yellow clear uEM yes |
| 208.4 | 98.0 | 0.9120 | 60 | same |

TABLE 13

Formula-70-EH6-28-5

| | | |
|---|---|---|
| NaCL 0.13% | | 33.3 |
| Soy Oil | | 33.3 |
| Ecosurf EH-6 | | 28.3 |
| Tegin ISO | 5 ml = 4.25 g | 4.25 |
| Total | | 99.15 |

Date: Jul. 10, 2009
Upon Mixing:
smooth white silky solution

| Cloud Point: TEMP F. | Temp C. | Cond, uS | Elapsed Time, min | State/Conditions |
|---|---|---|---|---|
| 96.8 | 35.6 | 166.50 | 0 | turning opaque |
| | 38.9 | 181.00 | | |
| | 39.8 | 186.60 | | more clear |
| 104.0 | 40.0 | 189.10 | | |
| | 41.0 | 210.90 | | almost clear |
| | 42.0 | 210.90 | | |
| 125.6 | 52.0 | 240.20 | | almost clear |
| | 55.0 | 297.80 | | |
| | 58.0 | 292.30 | | |
| 138.0 | 59.0 | 272.70 | | same |
| 141.0 | 60.0 | 272.70 | | |
| | 61.0 | 232.70 | | |
| | 62.0 | 232.70 | | |
| 146.0 | 63.0 | 231.70 | | |
| | 64.0 | 227.70 | | same |
| | 65.0 | 207.80 | | |
| | 66.6 | 194.30 | | |
| | 69.0 | 163.10 | | |
| 158.0 | 70.0 | 153.00 | | |
| | 71.4 | 98.320 | | more translucent |
| | 72.0 | 94.220 | | |
| | 74.0 | 81.620 | 44 | almost there u |
| | 75.0 | 67.240 | | |
| | 76.0 | 58.730 | | same |
| | 78.0 | 43.200 | | |
| 176.0 | 80.0 | 24.000 | | |
| | 81.8 | 17.480 | | same almost clear |
| | 82.0 | 16.400 | | |
| | 81.2 | 18.950 | | |
| | 78.0 | 40.410 | 51 | same |
| 170.6 | 77.0 | 40.410 | | Yes, u EM . . . ! |
| | 76.0 | 40.410 | | |
| | 75.0 | 19.580 | 57 | |
| | 75.0 | 19.580 | 57 | |
| | 74.0 | 3.8240 | 57 | |
| | 72.0 | 2.4800 | 61 | |
| | 71.0 | 1.8470 | 62 | |
| 158.0 | 70.0 | 1.2590 | 63 | |
| | 68.0 | 0.9210 | 65 | |
| | 66.0 | 0.8018 | 69 | |
| | 64.0 | 0.7206 | 70 | |
| | 63.0 | 0.6496 | 70 | |
| | 61.0 | 0.5949 | 72 | |

TABLE 13-continued

| | | |
|---|---|---|
| 57.5 | 0.5453 | 73 |
| 55.6 | 0.5409 | 77 |

Note:
unusual results . . . was almost uEM from the begin/onset of temps increasing then the kinetic parameter of formation was not enough to kick it into phase . . . until higher temps then remained in clear phase for an extended range . . .
Final Observation: remained in permanent uEM clear state . . . !
*Final product is a hydrolysis product like that of the EH-9/Tegin . . . next step is to optimize the Tegin amount . . . try 10 g next . . . !

TABLE 14

Formula-70-EH-3-28-5

| | | |
|---|---|---|
| NaCL 0.13% | | 33.3 |
| Soy Oil | | 33.3 |
| Ecosurf EH-3 | | 28.3 |
| Tegin ISO | 5 ml = 4.25 g | 4.25 |
| Total | | 99.15 |

Date: Jul. 10, 2009
Upon Mixing:
smooth white silky solution

| Cloud Point: TEMP F. | Temp C. | Cond, uS | Elapsed Time, min | State/Conditions |
|---|---|---|---|---|
| 77.0 | 25.0 | 239.000 | 0 | thick white milky solution |
| 78.8 | 26.0 | 150.600 | 5 | same |
| 80.0 | 26.5 | 156.700 | 7 | white liquid |
| 95.0 | 34.5 | 141.000 | 10 | chg in phase |
| 96.8 | 36.0 | 22.680 | 13 | went clear into u EM phase |
| 110.0 | 45.0 | 22.680 | 13 | same |
| 116.0 | 46.0 | 4.0990 | 14 | milky again out of phase |
| | | 2.0210 | 14 | same |
| | | 1.8690 | 14 | |
| | | 1.6900 | 14 | |
| | | 1.2950 | 15 | same |
| | | 1.1090 | 15 | same |
| 124.0 | 51.0 | 0.9716 | 17 | |
| 124.0 | 51.0 | 0.8976 | 18 | same |
| | | 0.8771 | 19 | |
| | | 152.900 | 35 | same |

Note:
Repeated increaseing and decreasing temperatures . . . always changing phase into u EM at optimal range ~39 C. +/− 1.0

TABLE 15

Formula-70-EH-9-23-10

| | | |
|---|---|---|
| NaCL 0.13% | | 33.3 |
| Soy Oil | | 33.3 |
| Ecosurf EH-9 | | 23.3 |
| Tegin ISO | 10 ml = 8.5 g | 8.50 |
| Total | | 98.40 |

Date: Jul. 13, 2009
Upon Mixing:

| Cloud Point: TEMP F. | Temp C. | Cond, uS | Elapsed Time, min | State/Conditions |
|---|---|---|---|---|
| 78.8 | 26.0 | 185.90 | 5 | thick white - not solid gel |
| 98.6 | 37.0 | 179.40 | 9 | add gentle heat |
| 116.6 | 47.0 | 195.80 | 10 | getting thinner |
| 136.4 | 58.0 | 225.00 | 14 | add remaining surf/oil 5 g-turning into more gel like |
| 134.6 | 57.0 | 264.20 | 15 | melt phase starting |
| | 58.0 | 200.80 | 16 | milky melting |

TABLE 15-continued

| 140.0 | 60.0 | 203.30 | 22 | fast chg of phase |
|---|---|---|---|---|
| 152.6 | 67.0 | 203.30 | 27 | clear on bottom |
| 159.8 | 71.0 | 198.80 | 30 | more clearing |
| 161.6 | 72.0 | 328.30 | 31 | same |
| 163.4 | 73.0 | 332.80 | 35 | same |
| 165.2 | 74.0 | 329.30 | 38 | all clearing |
| | 75.0 | 322.20 | 40 | same |
| 172.4 | 78.0 | 270.50 | 45 | foggy again |
| | 74.0 | 183.10 | 49 | clear on bottom |
| 168.8 | 76.0 | 183.10 | 49 | same |
| | 77.0 | 183.10 | 49 | more clearing |
| 173.0 | 78.0 | 183.10 | 50 | almost uEM . . . ! |
| | 79.0 | 183.10 | 51 | same |
| | 82.0 | 160.70 | 55 | same |
| | 83.0 | 155.80 | 56 | same |
| | 85.0 | 138.70 | 57 | |
| | 86.9 | 182.20 | 59 | |
| 188.6 | 87.0 | 168.60 | 60 | went to permanent u EM |

TABLE 16

Date: Jul. 20, 2009
TEST 24

| Formula-70-JLXL-70-23-10 | | | Notes: |
|---|---|---|---|
| NaCL 0.13% | | 33.3 | TITRATION METHOD . . . wt/ Tegin |
| Soy Oil | | 33.3 | Approx CL/Pt Test 13 was 76-82 C. range |
| Lutensol XL-70 | | 23.3 | At end went into permanent clear phase . . . ? |
| Tegin ISO | | 10.20 | |
| Total | | 100.10 | |

Date: Jul. 20, 2009
Upon Mixing:
Went into smooth milky white liquid/solution

| TEMP F. | Temp C. | Cond, uS | Elapsed Time, min | State/Conditions |
|---|---|---|---|---|
| 77.0 | 25.6 | 188.50 | 0 | added 4.24 g Tegin to initial mixture |
| 148.0 | 64.0 | 322.40 | 14 | Rapid clearing of mixture *added .85 g more of Teg |
| 153.0 | 67.0 | 458.30 | 16 | *added 1 ml = 0.85 g more of Tegin |
| 157.0 | 69.0 | 419.30 | 17 | all opaque phase chg/translucent |
| 164.0 | 73.0 | 386.40 | 19 | almost uEM phase chg/*added another 1 ml |
| 174.0 | 79.0 | 171.80 | 24 | *added 1 ml = 0.85 g more of Tegin |
| 179.0 | 82.0 | 68.74 | 29 | *added 1 ml = 0.85 g more of Tegin |
| 181.0 | 83.0 | 27.33 | 31 | Decreased temps to watch for phase chg |
| | 72.0 | | | Increase temps to watch for phase chg |
| | 76.0 | | | |
| | 71.0 | | uEM | *added 2 ml = 1.7 g Tegin *71 C. to 68 C. in phase |
| | 69.0 | | uEM | Range of phase ~69 C. to 73 C. . . . avg 71 C. |
| | 74 C. | | uEM | phase remains permanent 100% clear |

Table 17 summarizes all soybean oil microemulsion formation data with Ecosurf EH and Lutensol XL non-ionic extended surfactants, with and without co-surfactants. Table 18 separates those of the Ecosurf EH's, and Table 19 separates those of the Lutensol XL's. The data clearly show that Ecosurf EH's are preferred over Lutensol XL's, forming microemulsion at lower temp and shorter time. It is also clear that the incorporation of Tegin ISO and free fatty acid as co-surfactant helps, as highlighted in yellow in Table 18.

TABLE 17

MICROEMULSION TEST RESULTS Jul. 21, 2009
Monica Tindel-Koukal

| SURFACTANT | CO-SURFACTANT | ELAPSED TIME-min | TEMP-F. | TEMP-C. | DATE | Literat CloudPt | TEST # | MISC. | COMMENTS |
|---|---|---|---|---|---|---|---|---|---|
| Ecosurf EH-3 | | 81 | 197.6 | 92 | Jun. 4, 2009 | — | 1 | NaCl = 13.0% | No uEM |
| Ecosurf EH-6 | | 99 | 172.9 | 78 | Jun. 5, 2009 | 43 C. | 2 | NaCl = 13.0% | Perm. uEM |
| Ecosurf EH-9 | | 76 | 184.1 | 84.5 | Jun. 8, 2009 | 64 C. | 3 | NaCl = 13.0% | Perm. uEM |
| Ecosurf EH-9 | | 84 | 189.1 | 87.3 | Jun. 9, 2009 | | 4 | MgCl = 0.20% | Perm. uEM |
| Lutensol XL-40 | | 72 | 171.7 | 77.7 | Jun. 16, 2009 | — | 5 | NaCl = 0.13% | Perm. uEM |
| Lutensol XL-60 | | 80 | 175.0 | 79.0 | Jun. 16, 2009 | — | 6 | NaCl = 0.13% | Perm. uEM |
| Ecosurf EH-3 | | 84 | 185 | 85.3 | Jun. 22, 2009 | | 7 | | Perm. uEM |
| Ecosurf EH-6 | | 83 | 206 | 96 | Jun. 23, 2009 | | 8 | | Perm. uEM |
| Ecosurf EH-9 | | 90 | 212 | 99.8 | Jun. 24, 2009 | | 9 | | Perm. uEM |
| Lutensol XL-90 | | 96 | 200 | 93 | Jun. 29, 2009 | 69 C. | 10 | | Perm. uEM |
| Lutensol XL-100 | | 69 | 201 | 94 | Jun. 30, 2009 | 80 C. | 11 | | Perm. uEM |
| Lutensol XL-80 | | 104 | 210 | 99 | Jun. 30, 2009 | 56 C. | 12 | | Perm. uEM |
| Lutensol XL-70 | | 96 | 168 | 76 | Jul. 6, 2009 | — | 13 | | Perm. uEM |
| Ecosurf EH-9 (Repeat) | | 101 | 181 | 83 | Jul. 6, 2009 | | 14 | | Perm. uEM |
| Ecosurf EH-9 = 28.3 g | Tegin 5 ml = 4.25 g | 50 | 197 | 92 | Jul. 13, 2009 | | 15 | almost uEM ~79 C. | Perm. uEM |
| Ecosurf EH-6 = 28.3 g | Tegin 5 ml = 4.25 g | 52 | 170.6 | 77 | Jul. 10, 2009 | | 16 | | Perm. uEM |
| Ecosurf EH-3 | Tegin 5 ml = 4.25 g | 13 | 102 | 93 | Jul. 10, 2009 | | 17 | | Chg at ~39 C. In/Out * not perm |
| Ecosurf EH-9 | Tegin 10 ml = 8.5 g | 60 | 188.6 | 87 | Jul. 13, 2009 | | 18 | almost uEM ~78 C. | Perm. uEM |
| Ecosurf EH-6 = 23.3 g | Tegin 10 ml = 8.5 g | 12 | 140 | 60 | Jul. 13, 2009 | | 19 | | Chg at ~60 C. In/Out * not perm |
| EH-3 = 14.5 g/ EH-6 = 11.65 g | Tegin 7.5 ml = 6.38 g | 14 | 120 | 49 | Jul. 14, 2009 | | 20 | | Chg at ~49 C. In/Out * not perm |
| EH-3 = 14.3 g/ EH-6 = 14.00 g | Tegin 5 ml = 4.25 g | 18 | 134.6 | 57 | Jul. 14, 2009 | | 21 | | Chg at ~57 C. In/Out * not perm |
| EH-3 = 14.5 g/ EH-6 = 11.65 g | Tegin = 4.25 g | 16 | 117 | 47 | Jul. 16, 2009 | | 22 | Linoleic acid = 2 ml | CONVERT TO g |
| Ecosurf EH-9 = 18.3 g | Tegin = 15 g | 25 | 177.8 | 81 | Jul. 16, 2009 | | 23 | | Chg at ~81 C. In/Out * not perm |
| Lutensol-XL 70 = 23.3 g | Tegin = 10.2 g | — | 165 | 74 | Jul. 20, 2009 | — | 24 | | chg in/out ~74 C. . . . then perm. |
| NPE 9.5 = 1.243 g/ Oil = 16.5 g | 5 gr H2O = 82.3 g | — | 140 | 60 | Jul. 21, 2009 | | 25 | Ratio Test | *Cloudy opaque B4 and AF |
| EH-6 = 1.243 g/ Oil = 16.5 g | 5 gr H2O = 82.3 g | — | 140 | 60 | Jul. 21, 2009 | | 26 | Ratio Test | *slight uEM activity During |
| EH-6 = 0.91 g/ Tegin = 0.33 g | H2O = 82.3 g + Oil = 16.5 g | — | 140 | 60 | Jul. 22, 2009 | | 27 | Ratio Test | *Same |
| EH-3 = 0.55 g/ EH-6 = 0.53 g | H2O = 82.3 g + Oil = 16.5 g, Tegin = 0.162 g | | 140 | 60 | Jul. 22, 2009 | | 28 | Ratio Test | *All went into 3 phases upon cl/dwn |
| Yvonne Recipe | | | 140 | 60 | Jul. 22, 2009 | | 29 30 | Ratio Test | |
| NOTE * General Formula = 33.3% Soy Oil (Baker)/ 33.3% Salt-H2O/33.3% Surfactant = 99.9% | | | | | | | | | |

TABLE 18

ECOSURF - EH
MICROEMULSION TEST RESULTS
Monica Tinkel-Koukal

| SURFACTANT | CO-SURFACTANT | ELAPSED TIME-min | TEMP-F. | TEMP-C. | DATE | Literat CloudPt | TEST # | MISC. | COMMENTS |
|---|---|---|---|---|---|---|---|---|---|
| Ecosurf EH-3 | | 81 | 197.6 | 92 | Jun. 4, 2009 | — | 1 | NaCl = 13.0% | No uEM |
| Ecosurf EH-6 | | 99 | 172.9 | 78 | Jun. 5, 2009 | 43 C. | 2 | NaCl = 13.0% | Perm. uEM |
| Ecosurf EH-9 | | 76 | 184.1 | 84.5 | Jun. 8, 2009 | 64 C. | 3 | NaCl = 13.0% | Perm. uEM |
| Ecosurf EH-9 | | 84 | 189.1 | 87.3 | Jun. 9, 2009 | | 4 | MgCl = 0.20% | Perm. uEM |
| Ecosurf EH-3 | | 84 | 185 | 85.3 | Jun. 22, 2009 | | 7 | | Perm. uEM |
| Ecosurf EH-6 | | 83 | 206 | 96 | Jun. 23, 2009 | | 8 | | Perm. uEM |
| Ecosurf EH-9 | | 90 | 212 | 99.8 | Jun. 24, 2009 | | 9 | | Perm. uEM |
| Ecosurf EH-9 (Repeat) | | 101 | 181 | 83 | Jul. 6, 2009 | | 14 | | Perm. uEM |

TABLE 18-continued

ECOSURF - EH
MICROEMULSION TEST RESULTS
Monica Tinkel-Koukal

| SURFACTANT | CO-SURFACTANT | ELAPSED TIME-min | TEMP-F. | TEMP-C. | DATE | Literat CloudPt | TEST # | MISC. | COMMENTS |
|---|---|---|---|---|---|---|---|---|---|
| Ecosurf EH-9 = 28.3 g | Tegin 5 ml = 4.25 g | 50 | 197 | 92 | Jul. 13, 2009 | | 15 | almost uEM ~79 C. | Perm. uEM |
| Ecosurf EH-6 = 28.3 g | Tegin 5 ml = 4.25 g | 52 | 170.6 | 77 | Jul. 10, 2009 | | 16 | | Perm. uEM |
| Ecosurf EH-3 | Tegin 5 ml = 4.25 g | 13 | 102 | 93 | Jul. 10, 2009 | | 17 | | Chg at ~39 C. In/Out * not perm |
| Ecosurf EH-9 | Tegin 10 ml = 8.5 g | 60 | 188.6 | 87 | Jul. 13, 2009 | | 18 | almost u EM ~78 C. | Perm. uEM |
| Ecosurf EH-6 = 23.3 g | Tegin 10 ml = 8.5 g | 12 | 140 | 60 | Jul. 13, 2009 | | 19 | | Chg at ~60 C. In/Out * not perm |
| EH-3 = 14.5 g/ EH-6 = 11.65 g | Tegin 7.5 ml = 6.38 g | 14 | 120 | 49 | Jul. 14, 2009 | | 20 | | Chg at ~49 C. In/Out * not perm |
| EH-3 = 14.3 g/ EH-6 = 14.00 g | Tegin 5 ml = 4.25 g | 18 | 134.6 | 57 | Jul. 14, 2009 | | 21 | | Chg at ~57 C. In/Out * not perm |
| EH-3 = 14.5 g/ EH-6 = 11.65 g | Tegin = 4.25 g | 16 | 117 | 47 | Jul. 16, 2009 | | 22 | Linoleic acid = 2 ml | |
| Ecosurf EH-9 = 18.3 g | Tegin = 15 g | 25 | 177.8 | 81 | Jul. 16, 2009 | | 23 | | Chg at ~81 C. In/Out * not perm |

TABLE 19

LUTENSOL XL
MICRO
EMULSION TEST RESULTS
Monica Tindel-Koukal

| SURFACTANT | CO-SURFACTANT | ELAPSED TIME-min | TEMP-F. | TEMP-C. | DATE | Literat CloudPt | TEST # | MISC. | COMMENTS |
|---|---|---|---|---|---|---|---|---|---|
| Lutensol XL-40 | | 72 | 171.7 | 77.7 | Jun. 16, 2009 | — | 5 | NaCl = 0.13% | Perm. uEM |
| Lutensol XL-60 | | 80 | 175.0 | 79.0 | Jun. 16, 2009 | — | 6 | NaCl = 0.13% | Perm. uEM |
| Lutensol XL-90 | | 96 | 200 | 93 | Jun. 29, 2009 | 69 C. | 10 | | Perm. uEM |
| Lutensol XL-100 | | 69 | 201 | 94 | Jun. 30, 2009 | 80 C. | 11 | | Perm. uEM |
| Lutensol XL-80 | | 104 | 210 | 99 | Jun. 30, 2009 | 56 C. | 12 | | Perm. uEM |
| Lutensol XL-70 | | 96 | 168 | 76 | Jul. 6, 2009 | — | 13 | | Perm. uEM |
| Lutensol-XL 70 = 23.3 g | Tegin = 10.2 g | — | 165 | 74 | Jul. 20, 2009 | — | 24 | | chg in/out ~74 C. . . . then perm. |

(VI) Temperature Sensitivity

A series of tests was performed with varying levels of linker co-surfactant to determine if the temperature at which the microemulsion forms can be optimized for different systems. For each system, the temperature range at which a microemulsion is present was determined.

Figure 8:
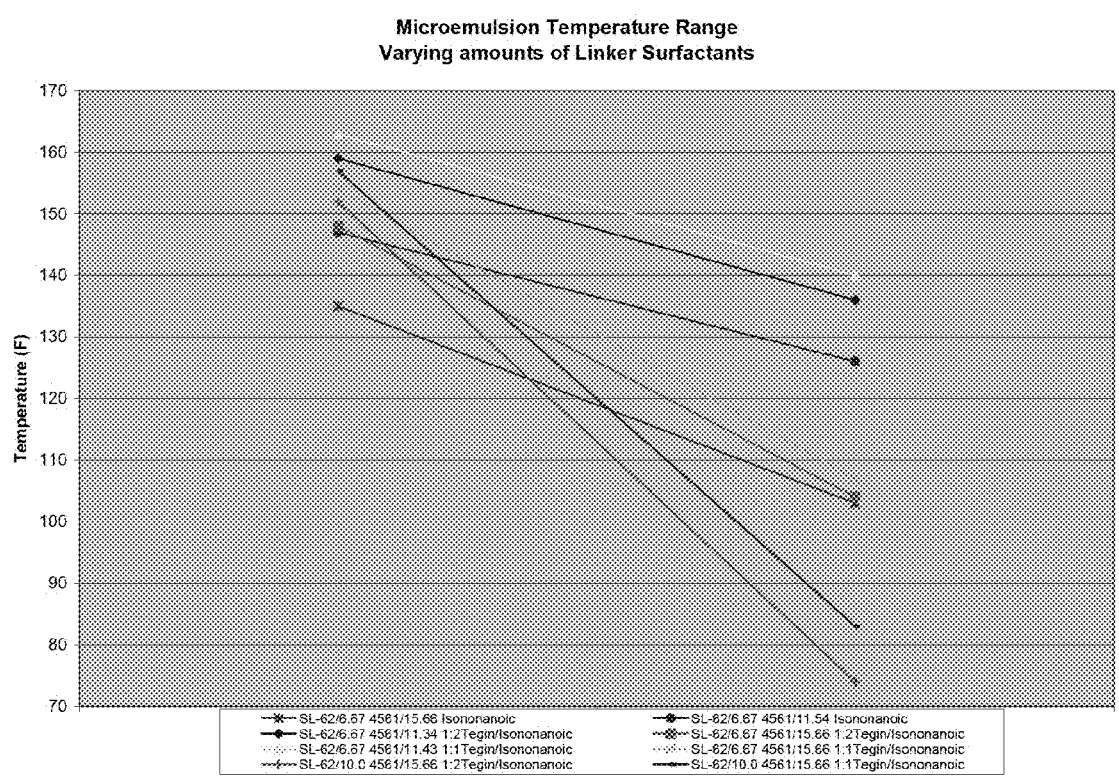
FIG. 8 is a graph showing the temperature sensitivity of various linker surfactants.

The systems can be optimized for both the temperature at which the microemulsion can be formed and the temperature range of microemulsion formation with varying amounts of linker surfactant. FIG. 8 shows the results of the temperature optimized microemulsions, as discussed above.

| | Formula | Soybean Oil | Plurafac SL-62 | Marlowet 4561 | Isononanoic Acid | Tegin ISO | Upper Limit | Lower Limit | Temp Range |
|---|---|---|---|---|---|---|---|---|---|
| | | | | (g) | | | (F.) | | |
| 1 | SL-62/6.67 4561/11.54 Isononanoic | 33.00 | 33.00 | 6.67 | 11.54 | 0 | 147 | 126 | 21 |
| 2 | SL-62/6.67 4561/15.66 Isononanoic | 33.00 | 33.00 | 6.67 | 15.66 | 0 | 135 | 103 | 32 |
| 3 | SL-62/6.67 4561/11.34 1:2 Tegin/Isononanoic | 33.00 | 33.00 | 6.67 | 3.78 | 7.56 | 159 | 136 | 23 |
| 4 | SL-62/6.67 4561/15.66 1:2 Tegin/Isononanoic | 33.00 | 33.00 | 6.67 | 5.22 | 10.44 | 148 | 104 | 44 |
| 5 | SL-62/6.67 4561/11.43 1:1 Tegin/Isononanoic | 33.00 | 33.00 | 6.67 | 5.72 | 5.72 | 163 | 140 | 23 |
| 6 | SL-62/6.67 4561/15.66 1:1 Tegin/Isononanoic | 33.00 | 33.00 | 6.67 | 7.83 | 7.83 | 154 | 107 | 47 |
| 7 | SL-62/10.0 4561/15.66 1:2 Tegin/Isononanoic | 33.00 | 33.00 | 10.00 | 5.22 | 10.44 | 152 | 74 | 78 |
| 8 | SL-62/10.0 4561/15.66 1:1 Tegin/Isononanoic | 33.00 | 33.00 | 10.00 | 7.83 | 7.83 | 157 | 83 | 74 |

(VII) Laundry Soil Removal

Figure 9:
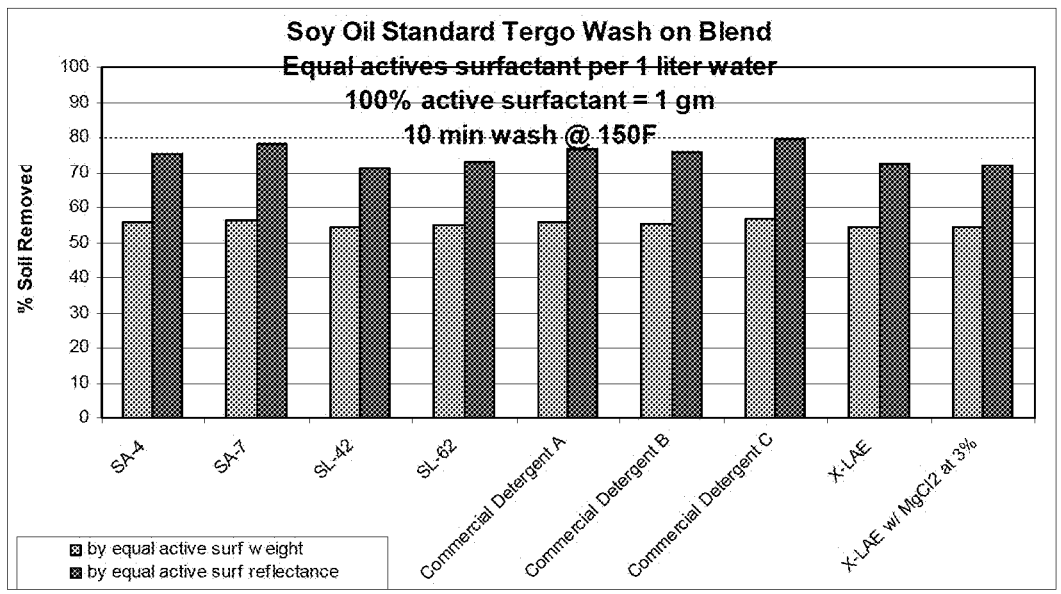
FIG. 9 shows the results of the soy oil tergo wash test comparing the extended chain nonionic surfactants with Commercial Detergent A, Commercial Detergent B, Commercial Detergent C, X-LAE, and X-LAE with $MgCl_2$.
Figure 10:
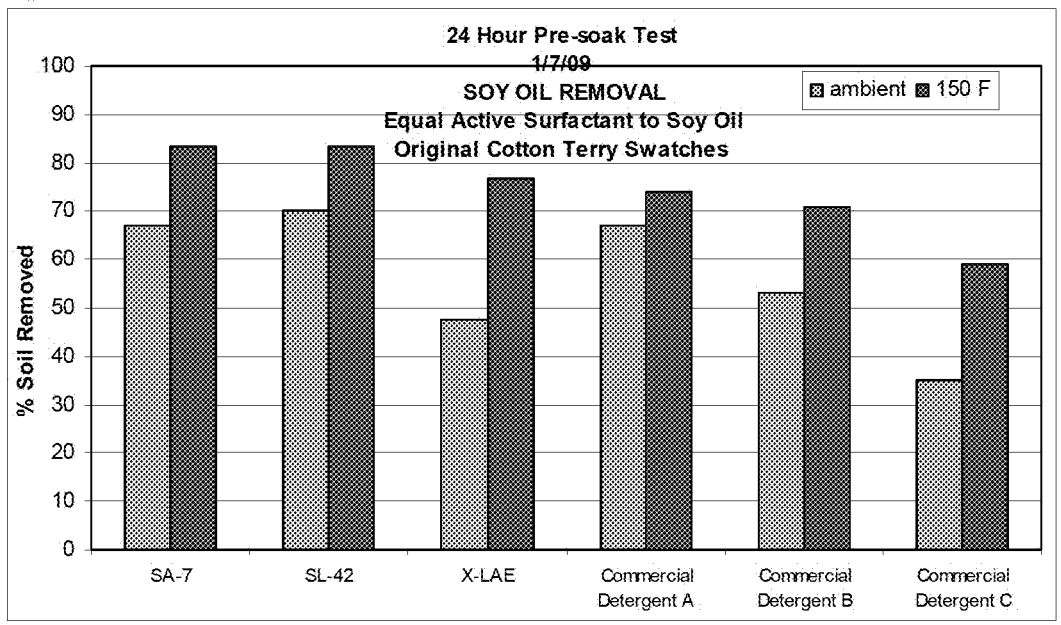
FIG. 10 shows the results of the 24 hour pretest of soy oil removal for SA-7, SL-42, X-LAE, Commercial Detergent A, Commercial Detergent B, and Commercial Detergent C.

In a series of tests, five nonionic extended surfactants (SA-4, SA-7, SL-42, SL-62, and X-LAE are compared to some regular non-ionic surfactant based systems with tergo screening method. Results are shown in FIG. 9. The results show roughly equal performance.

In a second series of tests, the comparison was made with a prespot/presoak method. In this method, the soiled swatch is prespoted or presoaked with the test surfactant or detergent at room temperature for 24 hours, followed by a water only wash at room temperature or 150 F. These results show that the extended surfactants, especially SA-7 and SL-42, perform better. The results are depicted graphically in

|  | % active surf | Soy oil, gm | Equal active surf, gm of product |
|---|---|---|---|
| X-LAE | 100% | 0.30 | 0.30 |
| SL-42 | 100% | 0.30 | 0.30 |
| SA-7 | 100% | 0.30 | 0.30 |
| Commercial Detergent B | 73.80% | 0.30 | 0.41 |
| Commercial Detergent A | 52.80% | 0.30 | 0.57 |
| Commercial Detergent C | 72.14% | 0.30 | 0.42 |

1. Soak original cotton/terry swatches in oil and surfactant/detergent X 24 hours at ambient temp.
2. Wash one-half of swatches X 5 minutes in 1 liter ambient DI water at 250 rpm.
3. Wash one-half of swatches X 5 minutes in 1 liter 150° F. DI water at 250 rpm.
4 Rinse X 2 minutes in ambient DI water Commercial Detergent A is an AE based detergent, Commercial Detergent B is an NPE based detergent, and Commercial Detergent C is an AE based detergent.

(VII) Compositions and Methods of Use:

In some applications, the formation of the non-trans fat oil microemulsions is the goal. For example, the formation of a triglyceride based or other oil based dry lube to be used for conveyor lubricant. Other examples include triglyceride or other oil based suntan lotion.

Many applications are based on cleaning of non-trans fat oil soils from substrate. In these applications, the cleaning compositions comprise the non-ionic extended surfactant portion and the linker surfactant portion. The linker surfactant portion comprises mono- and di-glycerides and/or fatty acid and fatty diacids.

What is claimed is:

1. A surfactant system for forming stable emulsions or microemulsions with oils comprising:
an extended chain nonionic surfactant having an intermediate polarity linking chain between a lipophilic segment and a hydrophilic segment of said surfactant, wherein said linking chain is selected from the group consisting of $(PO)_x$, $(EO)_x$, $(PO)_x(EO)_x$ and combinations thereof, wherein x is from 1 to 16, wherein said extended surfactant comprises a compound of formula:

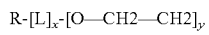

where R is a linear or branched, saturated or unsaturated, substituted or unsubstituted, aliphatic or aromatic hydrocarbon radical having from about 8 to 20 carbon atoms, L is a linking group, x is the chain length of the linking group ranging from 5-15, and y is the average degree of ethoxylation ranging from 1 to 5;
a linker co-surfactant selected from the group consisting of monoglycerides, diglycerides, fatty acids, fatty diacids and combinations thereof wherein said link co-surfactant has a small hydrophilic head and/or surfactants with twin or bulky hydrophobic tail(s);
wherein the system is capable of forming a stable emulsion or microemulsion with oils.

2. The surfactant system of claim 1 wherein said linker co-surfactant is a monoglyceride or diglyceride.

3. The surfactant system of claim 2 wherein said extended chain nonionic surfactant and linker co-surfactant are present in a weight percent ratio of about 7 to 1.

4. The surfactant system of claim 1 wherein said linker co-surfactant is a fatty acid or fatty diacid.

5. The surfactant system of claim 4 wherein said extended chain nonionic surfactant and linker co-surfactant are present in a weight percent ratio of about 2 to 1.

6. An emulsion or microemulsion comprising the surfactant system of claim 1 and an oil component selected from the group consisting of an oil, fatty acid, or triglyceride.

7. The emulsion or microemulsion of claim 6 wherein said oil is a vegetable oil.

8. The emulsion or microemulsion of claim 6 wherein said oil is a synthetic oil.

9. The emulsion or microemulsion of claim 6 wherein said oil is a triglyceride.

10. The emulsion or microemulsion of claim 6 wherein said oil is a non-trans fat.

11. The surfactant system of claim 1 wherein said emulsion or microemulsion is irreversible.

12. The surfactant system of claim 1 wherein said extended nonionic surfactant is one or more of the following:

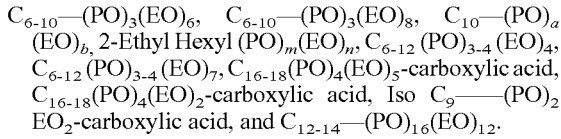

13. The surfactant system of claim 1 wherein said system is used as a pre-spotter.

14. A cleaning composition including the surfactant system of claim 1.

15. The cleaning composition of claim 14 wherein said cleaning composition is a hard surface cleaner.

16. The cleaning composition of claim 14 wherein said cleaning composition is a laundry detergent.

17. A method for removing a soil from a hard surface comprising applying a cleaning composition containing the surfactant system according to claim 1 to the hard surface and rinsing and/or wiping the cleaning composition from the hard surface.

18. A method for removing a soil from a soft surface comprising applying a cleaning composition containing the surfactant system according to claim 1 to the soft surface and rinsing and/or wiping the cleaning composition from the soft surface.

19. A method of laundering an article that is contacted with a non-trans fat, comprising:
providing a cleaning article that has been contacted with a non-trans fat;
washing the cleaning article;
rinsing the cleaning article;
drying the cleaning article; and
treating the cleaning article with an effective amount of a composition comprising a surfactant system according to claim 1, wherein the treating occurs prior to or during the washing step.

20. A method of neutralizing a non-trans fat from fire risk, comprising:
    treating the non-trans fat with an effective amount of the surfactant system of claim 1 so that an emulsion or microemulsion is formed with the non-trans fat.

21. The surfactant system of claim 1 wherein said surfactant system is essentially free of unreacted alcohols.

\* \* \* \* \*